(12) United States Patent
Simard

(10) Patent No.: US 8,569,377 B2
(45) Date of Patent: *Oct. 29, 2013

(54) METHODS FOR TREATING SPINAL CORD INJURY WITH A COMPOUND THAT INHIBITS A NCCA-ATP CHANNEL

(75) Inventor: J. Marc Simard, Baltimore, MD (US)

(73) Assignees: The United States of America as Represented by the Department of Veteran Affairs, Washington, DC (US); University of Maryland, Baltimore, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 12/964,018

(22) Filed: Dec. 9, 2010

(65) Prior Publication Data

US 2011/0092542 A1 Apr. 21, 2011

Related U.S. Application Data

(63) Continuation of application No. 11/229,236, filed on Sep. 16, 2005, now Pat. No. 7,872,048.

(60) Provisional application No. 60/610,758, filed on Sep. 18, 2004, provisional application No. 60/698,272, filed on Jul. 11, 2005.

(51) Int. Cl.
*A61K 31/64* (2006.01)
*A61K 31/435* (2006.01)
*A61K 31/196* (2006.01)
*A61K 31/415* (2006.01)

(52) U.S. Cl.
USPC .......... 514/592; 514/317; 514/563; 514/593; 514/604; 514/870; 514/401

(58) Field of Classification Search
None
See application file for complete search history.

(56) References Cited

U.S. PATENT DOCUMENTS

| | | |
|---|---|---|
| 5,047,429 A | 9/1991 | Nye |
| 5,166,162 A | 11/1992 | Masereel et al. |
| 5,215,985 A | 6/1993 | Murphy et al. |
| 5,236,932 A | 8/1993 | Greenfield et al. |
| 5,281,599 A | 1/1994 | Murphy et al. |
| 5,451,580 A | 9/1995 | Murphy et al. |
| 5,545,656 A | 8/1996 | Loose et al. |
| 5,677,344 A | 10/1997 | Greenfield et al. |
| 5,811,393 A | 9/1998 | Klagsbrun et al. |
| 5,849,796 A | 12/1998 | Gericke et al. |
| 5,916,871 A | 6/1999 | Johnson |
| 5,929,082 A | 7/1999 | Chambers et al. |
| 5,962,645 A | 10/1999 | Keay et al. |
| 6,043,224 A | 3/2000 | Lee et al. |
| 6,100,047 A | 8/2000 | Wilkison et al. |
| 6,156,522 A | 12/2000 | Keay et al. |
| 6,184,248 B1 | 2/2001 | Lee et al. |
| 6,187,756 B1 | 2/2001 | Lee et al. |
| 6,232,289 B1 | 5/2001 | Keay et al. |
| 6,242,200 B1 | 6/2001 | Wilkison et al. |
| 6,365,577 B1 | 4/2002 | Iversen ........................... 514/44 |
| 6,372,743 B1 | 4/2002 | Darrow et al. |
| 6,376,197 B1 | 4/2002 | Keay et al. |
| 6,469,055 B2 | 10/2002 | Lee et al. |
| 6,492,130 B1 | 12/2002 | Wilkison et al. |
| 6,492,339 B1 | 12/2002 | Sleevi et al. ..................... 514/25 |
| 6,511,989 B2 | 1/2003 | Heitsch et al. |
| 6,569,633 B1 | 5/2003 | Wilkison et al. |
| 6,569,845 B1 | 5/2003 | Futamura et al. |
| 6,596,751 B2 | 7/2003 | Fujita et al. |
| 6,610,746 B2 | 8/2003 | Fryburg et al. |
| 6,613,785 B2 | 9/2003 | Bril et al. |
| 6,679,859 B1 | 1/2004 | Keipert et al. |
| 7,877,048 B2 * | 1/2011 | Kitagawa ...................... 399/299 |
| 2001/0003751 A1 | 6/2001 | Terashita et al. |
| 2001/0016586 A1 | 8/2001 | Guitard et al. |
| 2002/0013268 A1 | 1/2002 | Fryburg et al. |
| 2002/0037928 A1 | 3/2002 | Jaen et al. |
| 2002/0065315 A1 | 5/2002 | Jensen et al. |
| 2002/0081306 A1 | 6/2002 | Elliott et al. |
| 2002/0094977 A1 | 7/2002 | Robl et al. |
| 2003/0215889 A1 | 11/2003 | Simard et al. |
| 2003/0216294 A1 | 11/2003 | Fryburg et al. |
| 2006/0100183 A1 | 5/2006 | Simard .......................... 514/171 |
| 2007/0203239 A1 | 8/2007 | Gehenne et al. |

FOREIGN PATENT DOCUMENTS

| | | |
|---|---|---|
| EP | 1782815 A1 | 5/2007 |
| JP | 2004-516236 | 6/2004 |
| WO | WO-01/54771 | 8/2001 |
| WO | WO-03/075933 A1 | 9/2003 |
| WO | WO-03/079987 | 10/2003 |
| WO | WO/2006/000608 | 1/2006 |
| WO | WO-2007 058902 | 5/2007 |
| WO | WO 2008/089103 | 7/2008 |

OTHER PUBLICATIONS

Gavin (1989. West J M. 151: 525-529).*
Vestergaard et al (2005. Diabetologia. 48: 1292-1299.*
Second Office Action, issued Jul. 30, 2010 (published Jul. 30, 2010) during the prosecution of Chinese Application No. 200580036055.7.
European Patent Office Communication Pursuant to Article 94(3) EPC issued Jan. 16, 2009, regarding EP Application No. 05 805 849.6-2123.
Simard et al (2007. Journal of Clinical Investigation. 117(8): 2105-2113).
Haider et al, 2007. The EMBO Journal. 26: 3749-3759.
Phillips, A., J Pharm Pharmacology 53: 1169-1174, 2001.
Vidal et al. 2005. European Journal of Cancer. 41: 2812-2818.

(Continued)

*Primary Examiner* — Zachary Howard

(57) ABSTRACT

The present invention is directed to therapeutic compositions targeting the $NC_{Ca\text{-}ATP}$ channel of an astrocyte, neuron or capillary endothelial cell and methods of using same. More specifically, antagonists of the $NC_{Ca\text{-}ATP}$ channel are contemplated. The compositions are used to prevent cell death and to treat secondary damage associated with spinal cord injury.

9 Claims, 17 Drawing Sheets

(56) References Cited

OTHER PUBLICATIONS

Schmitt et al, 2002 ("Endocrine and Metabolic Consequences of Spinal Cord Injuries", Chapter 18 in Spinal Cord Medicine: principles and practices. 2002). pp. 221-235.
Gribble et al, 2003. Diabetologia. 46: 875-891.
Office Action issued in Japanese Application No. 2007-532507, mailed Apr. 13, 2012.
Proks et al., "Inhibition of recombinant KATP channels by the antidiabetic agents midaglizole, LY397364 and LY389382," *European Journal of Pharmacology*, 452:11-19, 2002.
Lee, Yong Soo, et al., "In Vitro Antitumor Activity of Cromakalim in Human Brain Tumor Cells," Pharmacology (1994) vol. 49, pp. 69-74.
Crepel et al., "Glibenclamide depresses the slowly inactivating outward current ($I_D$) in hippocampal neurons," *Canadian Journal of Physiology and Pharmacology*, 70(2):306-307, 1992.
Gribble et al., "Sulfonylurea sensitivity of adenosine triphosphate-sensitive potassium channels from β cells and extrapancreatic tissues," *Metabolism*, 49(10:2):3-6, 2000.
Grijalva et al., "Efficacy and safety of 4-aminopyridine in patients with long-term spinal cord injury: a randomized, double-blind, placebo-controlled trial," *Pharmacotherapy*, 23(7):823-834, 2003.
Liu et al., "Suppression of hippocampus fos expression and activator protein-1 (AP-1) activity during focal cerebral ischemia using antisense strategy," *Stroke*, 26(1):182, 1995.
Office Action issued in Japanese Application No. 2007-532507, mailed Jun. 20, 2011 (and English language translation thereof).
Partial European Search Report issued in European Application No. 10010753.1, mailed Jul. 22, 2011.
Wickelgren, "Animal studies raise hopes for spinal cord repair," *Science*, 297(5579):178-181, 2002.
Yokoshiki et al., "Antisense oligodeoxynucleotides of sulfonylurea receptors inhibit ATP-sensitive $K^+$channels in cultured neonatal rat ventricular cells," *Eur. J. Physiol.*, 437:400-408, 1999.
Aguilar-Bryan et al., "Cloning of the beta cell high-affinity sulfonylurea receptor: a regulator of insulin secretion," *Science*, 268: 423-426, 1995.
Ahmad et al., "Mouse cortical collecting duct cells show nonselective cation channel activity and express a gene related to the cGMP-gated rod photoreceptor channel," *Proc. Nati. Acad. Sci. USA*, 89: 10262-10266, 1992.
Angel et al., "The binding site for [3H] glibenclamide in the rat cerebral cortex does not recognize K-channel agonists or antagonists other than sulphonylureas," *Fundam. Clin. Pharmacol*, 5(2): 107-15, 1991.
Armijo, "Advances in the physiopathology of epilegtogenesis: molecular aspects," *Rev. Neurol.*, 34(5): 409-29, 2002.
Auger, G. et al; Purification and Partial Characterization of a Hepatocyte Antiproliferative Glycopeptide, Journal of Cellular Biochemistry, (1989) vol. 40, pp. 439-451.
Ballerini, "Glial cells express multiple Atp binding cassette proteins which are involved in ATP release," *Neuroreport*, 13(14): 1789-92, 2002.
Bareyre et al., "Inflammation, degeneration and regeneration in the injured spinal cord: insights from DNA microarrays," *Trends Neurosci.*, 26(10): 555-563, 2003.
Bartholdi et al., "Expression of pro-inflammatory cytokine and chemokine mRNA upon experimental spinal cord injury in mouse: an in situ hybridization study," *Eur. J. Neurosci.*, 9(7): 1422-1438, 1997.
Baudelet et al., "Evidence for a Neuroprotective Effect of Pyrid-3-yl-sulphonyl-urea in Photochemically Induced Focal Ischaemia in Rats: Magnetic Resonance Imaging Evaluation," *J. Pharm. Pharmacol.*, 51: 967-970, 1999.
Beier-Holgersen, R., "The in vitro cytotoxicity of urine from patients with interstitial cystitis", Journal of Urology (Jan. 1994), vol. 151, pp. 206-207.
Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.

Champigny et al., "A voltage, calcium, and ATP sensitive non selective cation channel in human colonic tumor cells," *Biochem. Biophys. Res. Commun.*, 176: 1196-1203, 1991.
Chen et al, "Cell Swelling and a Nonselective Cation Channel Regulated by Internal CA2+ and ATP in Native Reactive Astrocytes from Adult Rat Brain," The Journal of Neuroscience vol. 21 No. 17, Sep. 1, 2001, pp. 6512-6521.
Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Chen et al., "Functional coupling between sulfonylurea receptor type 1 and a nonselective cation channel in reactive astrocytes from adult rat brain," *J. Neurosci.*, 23: 8568-8577, 2003.
Copin et al., "70-kDa heat shock protein expression in cultured rat astrocytes after hypoxia: regulatory effect of almitrine," *Neurochem. Res.*, 20(1): 11-15, 1995.
Csanady et al., "Ca(2+)- and voltage-dependent gating of Ca(2+)- and ATP-sensitive cationic channels in brain capillary endothelium," *Biophys. J.*, 85: 313-327, 2003.
Currie et al., "Benign focal ischemic preconditioning induces neuronal Hsp70 and prolonged astrogliosis with expression of Hsp27," *Brain Res.*, 863(1-2): 169-181, 2000.
Davies, "Insulin secretagogues," *Curr. Med. Res. Opin. 18 Suppl.*, 1: ss22-30, 2002.
Fujita et al., "Molecular aspects of ATP-sensitive K+ channels in the cardiovascular system and K+ channel openers," *Pharmacol. Ther.*, 85: 39-53, 2000.
Gopalakrishnan et al., "Pharmacological characterization of a 1,4-dihydropyridine analogue, 9-(3,4-dichorophenyl)-3,3,6,6-tetramethyl-3,4,6,7,9,10-hexahydro-1,8(2H,5H)-acridinedione (A-184209) as a novel K(ATP) channel inhibitor," *Br. J. Phannacol.*, 138(2): 393-99, 2003.
Gray et al., "Non-selective cation channel on pancreatic duct cells," *Biochem. Biophys. Acta*, 1029:33-42, 1990.
Gribble et al., "Differential selectivity of insulin secretagogues. Mechanisms, clinical implications, and drug interactions," *J. Diabetes Complications*, 17(2 Suppl): 11-5, 2003.
Gribble et al., "Tissue Specificity of Sulfonylureas: Studies on Cloned Cardiac and B-Cells K-ATP Channels," Diabetes, 47: 1412-1418, 1998.
Hambrock et al., "Four novel splice variants of sulfonylurea receptor 1," *Am. J. Physiol. Cell Physiol.*, 283: C587-0598, 2002.
Hernandez-Sanchez et al., "Mice transgenically overexpressing sulfonylurea receptor 1 in forebrain resist seizure induction and excitotoxic neuron death," *PNAS*, 98(6): 3549-3554, 2001.
Inagaki et al., "A family of sulfonylurea receptors determines the pharmacological properties of ATP-sensitive K+ channels," *Neuron*, 16: 1011-1017, 1996.
Isomoto et al., "A novel sulfonylurea receptor forms with BIR (Kir6.2) a smooth muscle type ATP-sensitive K+ channel," *J. Biol. Chem.*, 271: 24321-24324, 1996.
Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.
Kakimura et al., "Microglial activation and amyloid-beta clearance induced by exogenous heat-shock proteins," *FASEB J.*, 16(6): 601-603, 2002.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression asscoiated with interstitial cystitis or antiproliferative factor treatment, Physiol. Genomics (2003) vol. 14, pp. 107-115.
Keay, S., et al.; Current and future directions in diagnostic markers in interstitial cystitis, Intern'l J. of Urology (2003) vol. 10, pp. S27-S230.
Keay, S., et al.; Decreased in Vitro Proliferation of Bladder Epithelial Cells from Patients with Interstitial Cystitis, Urology (2003) vol. 61, pp. 1278-1284.

(56) References Cited

OTHER PUBLICATIONS

Kimelberg et al., "Astrocytic swelling in traumatic-hypoxic brain injury. Beneficial effects of an inhibitor of anion exchange transport and glutamate uptake in glial cells," *Mol. Chem. Neuropathol.*, 11(1): 1-31, 1989.
Koch et al., "Mechanism of shrinkage activation of nonselective cation channels in M-1 mouse cortical collecting duct cells," *J. Membr. Biol.*, 177(3): 231-42, 2000.
Koch et al., "Osmotic shrinkage activates nonselective cation (NSC) channels in various cell types," *J. Membr. Biol.*, 168(2): 131-39, 1999.
Lauritzen et al., "The potassium channel opener (-)-cromakalim prevents glutamate-induced cell death in hippocampal neurons," *J. Neurochem.*, 69(4): 1570-79, 1997.
Lee et al, "Upregulation of Phospolipase D in Astrocytes in Response to Transient Forebrain Ischemia," GLIA vol. 30, 2000, pp. 311-317.
Lee et al., "Differential neuroprotection from human heat shock protein 70 overexpression in in vitro and in vivo models of ischemia and ischemia-like conditions," *Exp. Neurol.*, 170(1): 129-139, 2001.
Lee et al., "Direct demonstration of sulphonylurea-sensitive KATP channels on nerve terminals of the rat motor cortex," *Br. J. Pharmacol.*, 115(3) 385-87, 1995.
Lee et al., "The high-affinity sulphonylurea receptor regulates KATP channels in nerve terminals of the rat motor cortex," *J. Neurochem.*, 66(6): 2562-71, 1996.
Liu et al., "Tenidap, a novel anti-inflammatory agent, is an opener of the inwardly rectifying K+ channel hKir2.3," *Eur. J. Pharmacol.*, 435(2-3): 153-60, 2002.
Matz et al., "Heme-oxygenase-1 induction in glia throughout rat brain following experimental subarachnoid hemorrhage," *Brain Res.*, 713(1-2): 211-222, 1996.
Mautes et al., "Co-induction of HSP70 and heme oxygenase-1 in macrophages and glia after spinal cord contusion in the rat," *Brain Res.*, 883(2): 233-237, 2000.
Mautes et al., "Sustained induction of heme oxygenase-1 in the traumatized spinal cord," *Exp. Neurol.*, 166(2): 254-265, 2000.
Mest et al., "Glucose-induced insulin secretion is potentiated by a new imidazoline compound," *Naunyn Schmledebergs Arch. Pharmacol.*, 364(1): 47-52, 2001.
Nichols et al., "Adenosine diphosphate as an intracellular regulator of insulin secretion," *Science*, 272: 1785-1787, 1996.
Ono et al., "ATP and calcium modulation of nonselective cation channels in IMCD cells," *Am. J. Physiol.*, 267: F558-F565, 1994.
Papadopoulos et al., "Over-expression of HSP-70 protects astrocytes from combined oxygen-glucose deprivation," *Neuroreport*, 7(2): 429-432, 1996.
Parsons, C.L., et al., "Role of Toxic Urine in Interstitial Cystitis", Journal of Urology (1990) vol. 143, p. 373A.
Perillan et al., "Inward Rectifier K+ Channel Kir2.3 (IRK3) in Reactive Astrocytes from Adult Rat Brain," *GLIA*, 31: 181-192, 2000.
Perillan et al., "K+ Inward Rectifier Currents in Reactive Astrocytes from Adult Rat Brain," *GLIA*, 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," *J. Biol. Chem.*, 277: 1974-1980, 2002.
Popp et al, "A Calcium and ATP Sensitive Nonselective Cation Channel in the Antiluminal Membrane of Rat Cerebral Capillary Endothelial Cells," Biochimica et Biophysica Acta vol. 1108, 1992, pp. 59-66.
Proks et al., "Sulfonylurea stimulation of insulin secretion," *Diabetes*, 51(Suppl. 3): S368-76, 2002.
Rae et al., "A non-selective Cation Channel in Rabbit Corneal Endothelium Activated by Internal Calcium and Inhibited by Internal ATP," *Exp. Eye. Res.*, 50: 373-384, 1990.
Rashid, H., et al; Interstitial cystitis antiproliferative factor (APF) as a cell-cycle modulator, BMC Urology (2004) 4:3, pp. 1-5.
Regan et al., "Heme oxygenase-1 induction protects murine cortical astrocytes from hemoglobin toxicity," *Neurosci. Lett.*, 282(1-2): 1-4, 2000.

Schroder et al., "AMPA receptor-mediated modulation of inward rectifier K+ channels in astrocytes of couse hippocampus," *Mol. Cell Neurosci.*, 19(3): 447-8, 2002.
Schubert et al., "Cascading glia reactions: a common pathomechanism and its differentiated control by cyclic nucleotide signaling," *Ann. N.Y. Acad. Sci.*, 903: 24-33, 2000.
Shyng et al., "Regulation of KATP channel activity by diazoxide and MgADP. Distinct functions of the two nucleotide binding folds of the sulfonylurea receptor," *J. Gen. Physiol.*, 110: 643-654, 1997.
Simard et al., "Regulation by sulfanylurea receptor type 1 of a nonselective cation channel involved in cytotoxic edema of reactive astrocytes," *J. Neurosurg. Anesthesiol.*, 16(1): 98-9, 2004.
Song et al., "GeneChip analysis after acute spinal cord injury in rat," *J. Neurochem.*, 79(4): 804-815, 2001.
Sturgess et al., "Calcium and ATP regulate the activity of a nonselective cation channel in a rat insulinoma cell line," *Pflugers Arch.*, 409: 607-615, 1987.
Verkhratsky et al., "Ion channels in glial cells," *Brain Res. Rev.*, 32: 380-412, 2000.
Xu et al., "HSP70 protects murine astrocytes from glucose deprivation injury," *Neurosci. Lett.*, 224(1): 9-12, 1997.
Zhang, C., et al; Comparison of APF Activity and Epithelial Growth Factor Levels in Urine from Chinese, African-American, and White American Patients with Intestitial Cystitis, Urology (2003) vol. 61, pp. 897-901.
Gagliardino, J.J. et al.; "Inhibitory Effect of Sulfonylureas on Protein Phosphatase Activity in Rat Pancreatic Islets"; Acta Diabetol (1997) 34:6-9; Springer-Verlang 1997.
Rosenberg, Gary A.; "Ischemic Brain Edema"; Progress in Cardiovascular Diseases, vol. 42, No. 3 (Nov./Dec.), 1999: pp. 209-216.
Medline Plus ® Merriam Webster Medical Dictionary, main entry: par.en.ter.al, online <htt•://vvww2.merriam-webster.com/cgi-bin/mwmednlm; 2005; 1 page.
Supplementary European Search Report issued Jun. 19, 2008 during the prosecution of European Application No. 03 71 8003.
Lee et al., "In vitro Antitumor of Cromakalim in Human Brain Tumor Cells," *Pharmacology*, 49: 69-74, 1994.
European Patent Office Communication pursuant to Article 94(3) EPC, issued Dec. 10, 2008, during the prosecution of European Patent Application No. 05 812 199.7-2123.
Canadian Office Action issued Nov. 4, 2009 during the prosecution of Canadian Patent Application No. 2,477,812.
Khan Hussein Hamed, et al.; "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Rothstein et al, "Neuroprotective strategies in a model of chronic glutamate-mediated motor neuron toxicity," J Neurochem. Aug. 1995;65(2):643-51.
Israel Office Action, issued Feb. 15, 2010 (published Feb. 15, 2010) during the prosecution of International Application No. 181740.
Sang et al., "ATP sensitive potassium channels are involved in the protective effect of ischemic preconditioning on spinal cord in rabbits"; Chinese Pharmacological Bulletin, 2003, Issue 12, 1362-1365.
Notification of the First Office Action issued Jan. 22, 2010 during prosecution of Chinese Patent Aplication No. 200580036055.7 (English Translation).
Japanese Office Action, issued in Japanese Patent Application No. 2007-532321, mailed Apr. 22, 2011.
PCT International Preliminary Report on Patentability, issued in International application No. PCT/US2009/057111, dated Mar. 31, 2011.
Corrected International Search Report issued Sep. 18, 2008 during the prosecution of International Application No. PCT/US07/62392.
International Preliminary Report on Patentability issued Oct. 21, 2008 during the prosecution of International Application No. PCT/US07/62392.
No author named; APO-GLIBENCLAMIDE Data Sheet, Medsafe (New Zealand Medicines and Medical Devices Safety Authority), published Jun. 16, 1999, 6 pages; online <http://www.medsafe.govt.nz/Profs/DataSheet/a/Apoglibenclamidetab.htm>.

(56) References Cited

OTHER PUBLICATIONS

Slikker et al., "Session IV: Models of Neurotoxicity and Neuroprotection, Questions for Dr. Banik", Ann NY Acad Sci; 2003; 993; 159-160.

Sribnick et al., "Estrogen as a Neuroprotective Agent in the Treatment of Spinal Cord Injury", Ann. N.Y. Acedr, Sci., vol. 993;. 2003;125-133.

Supplementary European Search Report issued during the prosecution of European Application EP 05 81 1299, Oct. 12, 2008.

Weih et al., "Sulfonylurea Drugs Do Not Influence Initial Stroke Severity and In-Hospital Outcome in Stroke Patients With Diabetes", Stroke. 2001;32:2029-2032.

Written Opinion issued Sep. 18, 2008 during the prosecution of International Application No. PCT/US07/62392.

Yune et al., "Systemic Administration of 17β-Estradiol Reduces Apoptotic Cell Death and Improves Functional Recovery following Traumatic Spinal Cord Injury in Rats", Journal of Neurotrauma. Mar. 1, 2004, 21(3): 293-306.

\* cited by examiner

METHODS FOR TREATING SPINAL CORD INJURY WITH A COMPOUND THAT INHIBITS A NCCA-ATP CHANNEL

CROSS-REFERENCE TO RELATED APPLICATIONS

This Application is a continuation application of U.S. application Ser. No. 11/229,236, filed Sep. 16, 2005 now U.S. Pat. No. 7,872,048, which claims priority to U.S. Provisional Application Nos. 60/610,758 filed Sep. 18, 2004 and 60/698,272 filed Jul. 11, 2005, all of which applications are incorporated herein by reference in their entirety.

STATEMENT REGARDING FEDERALLY SPONSORED RESEARCH OR DEVELOPMENT

This invention was made with government support under Grant No. NS048260 awarded by the National Institutes of Health. The government has certain rights in the invention.

STATEMENT REGARDING OTHER SPONSORED RESEARCH OR DEVELOPMENT

This invention was made in part with support under a grant from the Christopher Reeves Paralysis Foundation (CRPF). The CRPF may have certain rights in the invention.

TECHNICAL FIELD

The present invention is directed to fields of cell biology, physiology and medicine. More specifically, the present invention addresses novel methods of treating a patient comprising administering a therapeutic compound that targets a unique non-selective cation calcium-ATP channel ($NC_{Ca-ATP}$ channel) found in astrocytes. In specific embodiments, the therapeutic compound is an antagonist, and uses thereof in therapies, such as treatment of spinal cord injury, benefiting from blocking and/or inhibiting the $NC_{Ca-ATP}$ channel. Compositions comprising of the $NC_{Ca-ATP}$ channel are also contemplated.

BACKGROUND OF THE INVENTION $NC_{Ca-ATP}$ Channel

A unique non-selective monovalent cationic ATP senstive channel ($NC_{Ca-APT}$ channel) was identified first in native reactive astrocytes (NRAs) and later, as described herein, in neurons and capillary endothelial cells after stroke or traumatic brain injury (See, International application WO 03/079987 to Simard et al., and Chen and Simard, 2001, each incorporated by reference herein in its entirety). The $NC_{CaATP}$ channel is thought to be a heteromultimer structure comprised of sulfonylurea receptor type 1 (SUR1) regulatory subunits and pore-forming subunits, similar to the $K_{ATP}$ channel in pancreatic β cells (Chen et al., 2003). The pore-forming subunits of the $NC_{Ca-ATP}$ channel remain uncharacterized.

SUR imparts sensitivity to antidiabetic sulfonylureas such as glibenclamide and tolbutamide, and is responsible for activation by a chemically diverse group of agents termed "K+ channel openers" such as diazoxide, pinacidil and cromakalin (Aguilar-Bryan et al., 1995; Inagaki et al., 1996; Isomoto et al., 1996; Nichols et al., 1996; Shyng et al., 1997). In various tissues, molecularly distinct SURs are coupled to distinct pore-forming subunits to form different $K_{ATP}$ channels with distinguishable physiological and pharmacological characteristics. The $K_{ATP}$ channel in pancreatic β cells is formed from SUR1 linked with Kir6.2, whereas the cardiac and smooth muscle $K_{ATP}$ channels are formed from SUR2A and SUR2B linked with Kir6.2 and Kir6.1, respectively (Fujita et al., 2000). Despite being made up of distinctly different pore-forming subunits, the $NC_{Ca-ATP}$ channel is also sensitive to sulfonylurea compounds.

Also, unlike the $K_{ATP}$ channel, the $NC_{Ca-ATP}$ channel conducts sodium ions, potassium ions, cesium ions and other monovalent cations with near equal facility (Chen and Simard, 2001) suggesting further that the characterization, and consequently the affinity to certain compounds, of the $NC_{Ca-ATP}$ channel differs from the $K_{ATP}$ channel.

Other nonselective cation channels that are activated by intracellular $Ca^{2+}$ and inhibited by intracellular ATP have been identified but not in astrocytes. Further, the $NC_{Ca-ATP}$ channel expressed and found in astrocytes differs physiologically from the other channels with respect to calcium sensitivity and adenine nucleotide sensitivity (Chen et al., 2001).

Other nonselective cation channels that are activated by intracellular $Ca^{2+}$ and inhibited by intracellular ATP have been identified in endothelial cells (Csanady and Adam-Vizi, *Biophysical Journal*, 85:313-327, 2003), but these channels are not regulated by SUR1 and are not inhibited by glibenclamide.

Spinal Cord Injury

A contusion injury to the spinal cord is often worsened by secondary damage from tissue inflammation and swelling. Secondary injury that expands the region of irreversible damage should, in principal, be preventable since it occurs in delayed fashion while under medical care, but effective treatments are not yet available. Secondary injury typically involves a zone of potentially viable tissue, called the penumbra, that surrounds the initial injury. Viability of neural tissues in the penumbra is precarious, and those tissues can easily succumb and die.

Changes in gene expression related to inflammation are among the earliest and strongest responses following spinal cord injury (Bareyre and Schwab, 2003; Bartholdi and Schwab, 1997).

An inflammatory response is necessary for resolution of the pathogenic event, but bystander or collateral tissue damage is caused by the toxic nature of many of its by-products. It is generally recognized that inflammation can be deleterious because cytotoxic agents such as TNFα and NO may be released, and because inflammation promotes formation of edema and swelling, which in turn contribute to tissue ischemia. Thus, a strong inflammatory response can cause expansion of the original zone of tissue death. In contrast, ameliorating the inflammatory response can diminish the overall extent of damage.

One of the most potent stimulators of inflammation in spinal cord injury is blood that extravasates from fractured capillaries following injury. Blood is universally held to be highly toxic to central nervous system tissues, include spinal cord.

Cells die by apoptosis and necrosis. The distinction is important, not so much for cells that die, but for cells in surrounding tissues—the penumbra—that may survive, albeit tenuously at first. Necrotic death incites an inflammatory response, whereas apoptotic death does not. Molecular mechanisms responsible for inflammation following necrotic cell death are not fully understood, but it is likely that necrotic death, unlike apoptotic death, is accompanied by release of intracellular molecules when cell membranes lyse. These intracellular molecules, when released, activate other cells, notably microglia, whose activation results in expression of chemokines that in turn attract inflammatory cells. Thus, a logical therapeutic goal is to reduce necrosis, even if only to convert it to apoptosis, to reduce the release of intracellular molecules that initiate inflammation.

An important class of intracellular molecules that can initiate inflammation in necrotic death is heat shock proteins (HSP). Injury to the spinal cord causes activation of astrocytes and up-regulation of developmentally regulated intracellular proteins, including vimentin, nestin and HSP. HSP-32 and HSP-70 are of special interest because they are up-regulated in spinal cord injury (Song et al., 2001; Mautes et al., 2000; Mautes and Noble, 2000). In astrocytes, HSP-32 (heme oxygenase-1) is induced by blood and blood products, and HSP-70 is induced by hypoxia or glucose deprivation (Regan et al., 2000; Matz et al., 1996; Lee et al., 2001; Currie et al., 2000; Xu and Giffard, 1997; Papadopoulos et al., 1996; Copin et al., 1995).

HSP-70 and HSP-32 activate microglia in vivo, (Kakimura et al., 2002) and activated microglia, in turn, release inflammatory chemokines that attract macrophages and polymorphonuclear leukocytes (PMNs). Thus, deleterious pathological events leading to inflammation-mediated secondary injury may originate, in part, with necrotic death of astrocytes and release of HSPs as well as from extravasated blood. Therefore, the present invention is directed to decreasing necrotic death of reactive astrocytes and to reducing extravasation of blood as an improved therapeutic strategy to treat spinal cord injury.

BRIEF SUMMARY OF THE INVENTION

The present invention is directed to therapeutic compositions comprising an antagonist of a $NC_{Ca\text{-}ATP}$ channel of neuronal cell, a neuroglia cell or an endothelial cell.

The present invention is directed to methods of reducing spinal cord injury in a patient in need thereof comprising administering an antagonist of a $NC_{Ca\text{-}ATP}$ channel of a neuronal cell, neuroglia cell or an endothelial cell. The antagonist inhibits (closes, blocks, deactivates, decreases biological activity) the $NC_{Ca\text{-}ATP}$ channel. The spinal cord injury may comprises a contusion on the spinal cord.

One embodiment of the present invention comprises a method of treating a subject suffering from a spinal cord injury comprising administering to the subject a compound effective to inhibit a $NC_{Ca\text{-}ATP}$ channel in a neuronal cell, a neuroglia cell, a neural endothelial cell or a combination thereof. The compound effectively inhibits the $NC_{Ca\text{-}ATP}$ channel by closing, blocking, partially blocking, and/or deactivating the channel thereby decreasing the Na+ influx, as well as other monovalent ion influx, into the cell, decreasing the accumulation of water in the cell thereby decreasing cell swelling. Thus, the compound of the present invention reduces, decreases or inhibits the activation of the $NC_{Ca\text{-}ATP}$ channel which reduces an influx of sodium ions ($Na^+$) thereby reducing and/or preventing or lessening the depolarization of the cell.

The subject can comprise a subject suffering from a spinal injury or a subject at risk for a spinal injury. Subjects at risk can include those subjects that are undergoing a surgical treatment and/or a radiation treatment. Other subjects at risk can include subjects having a spinal condition, for example, segmental deformities, cord compressions caused by any known type of disease or infection. For example, Cushing's syndrome can result in a growth of epidural fat tissue that compresses the spinal cord. Other diseases could include arthritic diseases of the spine.

The composition of the present invention may be delivered alimentary or parenterally. Examples of alimentary administration include, but are not limited to orally, buccally, rectally, or sublingually. Parenteral administration can include, but are not limited to intramuscularly, subcutaneously, intraperitoneally, intravenously, intratumorally, intraarterially, intraventricularly, intracavity, intravesical, intrathecal, or intrapleural. Other modes of administration may also include topically, mucosally (i.e., intranasally), or transdermally.

An effective amount of an antagonist of $NC_{Ca\text{-}ATP}$ channel that may be administered to a cell includes a dose of about 0.0001 nM to about 2000 µM. More specifically, doses to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000 µM; about 1000 µM to about 1500 µM and about 1500 µM to about 2000 µM. Of course, all of these amounts are exemplary, and any amount in-between these points is also expected to be of use in the invention.

An effective amount of an antagonist of the $NC_{Ca\text{-}ATP}$ channel or related-compounds thereof as a treatment varies depending upon the host treated and the particular mode of administration. In one embodiment of the invention the dose range of the antagonist of the $NC_{Ca\text{-}ATP}$ channel or related-compounds thereof will be about 0.01 µg/kg body weight to about 20,000 µg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an antagonist of $NC_{Ca\text{-}ATP}$ channel or related-compounds thereof.

The $NC_{Ca\text{-}ATP}$ channel is blocked or deactivated or inhibited by antagonists of type 1 sulfonylurea receptor (SUR1) and opened by SUR1 activators. More specifically, the antagonists of type 1 sulfonylurea receptor (SUR1) include blockers of $K_{ATP}$ channels and the SUR1 activators include activators of $K_{ATP}$ channels. More specifically, the $NC_{Ca-ATP}$ channel of the present invention has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca-ATP}$ channel is also inhibited by cytoplasmic ATP in a physiological concentration range, where the concentration range is from $10^{-1}$ to 10 M. The $NC_{Ca-ATP}$ channel is also permeable to the following cations; $K^+$, $Cs^+$, $Li^+$, $Na^+$; to the extent that the permeability ratio between any two of the cations is greater than 0.5 and less than 2.

The channel can be inhibited (closed, deactivated, blocked, partially inhibited or blocked, etc.) by an $NC_{Ca-ATP}$ channel inhibitor, an $NC_{CaATP}$ channel blocker, a type 1 sulfonylurea receptor (SUR1) antagonist, SUR1 inhibitor, or a compound capable of reducing the magnitude of membrane current through the channel. The antagonist of a type 1 sulfonylurea receptor includes a sulfonylurea compound, a benzamido derivative or an imidazoline derivative, in certain aspects. Benzamido derivatives such as repaglinide, nateglinide, and meglitinide represent a class of insulin secretagogues that bind to the SUR. More specifically, the SUR1 antagonist is selected from the group consisting of glibenclamide, tolbutamide, repaglinide, nateglinide, meglitinide, midaglizole, LY397364, LY389382, gliclazide (also known in the art as glyclazide), glimepiride, estrogen, estrogen-related compounds (estradiol, estrone, estriol, genistein, non-steroidal estrogen (e.g., diethystilbestrol), phytoestrogen (e.g., coumestrol), zearalenone, etc.), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2[5-chloro-O-anisamido)ethyl] phenyl]sulfonyl]-3-cyclohexyl-3-urea); chloropramide (1-[[(p-chlorophenyl)sulfonyl]-3-propylurea; glipizide (1-cyclohexyl-3[[p-[2(5-methylpyrazine carboxamido)ethyl] phenyl]sulfonyl]urea); or tolazamide(benzenesulfonamide-N-[[(hexahydro-1H-azepin-1yl)amino]carbonyl]-4-methyl).

In certain embodiments, the amount of the SUR1 antagonist administered to the subject is in the range of about 0.0001 μ/kg/day to about 20 mg/kg/day, about 0.01 μg/kg/day to about 100 μg/kg/day, or about 100 μg/kg/day to about 20 mg/kg/day. Still further, the SUR1 antagonist may be administered to the subject in the from of a treatment in which the treatment may comprise the amount of the SUR1 antagonist or the dose of the SUR1 antagonist that is administered per day (1, 2, 3, 4, etc.), week (1, 2, 3, 4, 5, etc.), month (1, 2, 3, 4, 5, etc.), etc. Treatments may be administered such that the amount of SUR1 antagonist administered to the subject is in the range of about 0.0001 μg/kg/treatment to about 20 mg/kg/treatment, about 0.01 μg/kg/treatment to about 100 μg/kg/treatment, or about 100 μg/kg/treatment to about 20 mg/kg/treatment.

In certain embodiments, the antagonist treats adverse conditions associated with cytotoxic and ionic edema of the central nervous system. Such conditions include trauma, spinal cord injury, namely secondary neuronal injury, for example, but not limited to hemorrhagic conversion, immune system reactions, oxidative damage, calcium and excitotoxicity, necrosis and apoptosis, and/or axon damage. The protection via deactivation and/or inhibition of the $NC_{Ca-ATP}$ channel is associated with a reduction in edema, reduction in cell death, reduction in extrvasation of blood in the injury site, reduction in the generation of reactive oxidative species, reduction in inflammation or the inflammatory response, and/or reduction in hemorrhagic conversion. Thus, the compound of the present invention reduces these symptoms compared to the level of the symptoms if the compound was not administered.

In certain embodiments, the $NC_{Ca-ATP}$ channel is blocked, inhibited, or otherwise is decreased in activity such that the ion $Na^+$ and/or other monovalent ions influx through the channel is reduced, ceased, decreased and/or stopped. The antagonist may prevent or lessen the depolarization of the cells thereby lessening cell swelling due to osmotic changes that can result from $Na^+$ influx and depolarization of the cells. Thus, inhibition of the $NC_{Ca-ATP}$ channel can reduce cytotoxic edema and death of cells, for example, necrotic death of cells. Thus, the antagonist of the present invention can be used to reduce secondary damage associated with the spinal cord injury.

Still further, the present invention may comprise methods to reduce or decrease the morbidity of a subject suffering from a spinal cord injury comprising administering an effective amount of a compound to inhibit and/or deactivate the $NC_{Ca-ATP}$ channel in a neuronal cell, a neuroglia cell, an endothelial cell or a combination thereof. A reduction in morbidity results in a improvement in physical and/or movement outcomes and/or sensation of the subject. Thus, an increase in the movement range and/or an increase in the sensation of the subject is an indicator that morbidity is reduced. In further embodiments, an increase in the physical well-being of the subject is also an indicator that the morbidity of the subject is reduced.

Still further, the present invention can comprise a method of reducing the blood and/or hemoglobin concentration in or near or surrounding the contusion site of a subject suffering a spinal cord injury comprising administering an effective amount of a compound to inhibit the $NC_{Ca-ATP}$ channel in a neuronal cell, a neuroglia cell, an endothelial cell or a combination thereof.

Yet further, another embodiment comprises a method of reducing the lesion size of a spinal cord injury in a subject comprising administering an effective amount of a compound to inhibit the $NC_{Ca-ATP}$ channel in a neuronal cell, a neuroglia cell, an endothelial cell or a combination thereof. A reduction in the lesion size reduces the likelihood of contralateral involvement.

Another embodiment of the present invention comprises increase or improving the preservation of myelinated long tracts comprising administering an effective amount of a compound to inhibit the $NC_{Ca-ATP}$ channel in a neuronal cell, a neuroglia cell, an endothelial cell or a combination thereof.

Still further, another embodiment of the present invention comprises the method of decreasing the up-regulation of GFAP in a subject suffering from a spinal cord injury comprising administering an effective amount of a compound to inhibit the $NC_{Ca-ATP}$ channel in a neuronal cell, a neuroglia cell, an endothelial cell or a combination thereof.

Yet further, another embodiment comprises a method of reducing extravasation of blood from a spinal cord injury comprising administering an effective amount of a compound to inhibit the $NC_{Ca-ATP}$ channel in a neuronal cell, a neuroglia cell, an endothelial cell or a combination thereof. The subject may be a subject that is suffering from a spinal cord injury or may be at risk for a spinal cord injury, for example a subject undergoing surgery or radiation. Thus, the compound may be administered before, during or after a surgical and/or radiation treatment.

Another embodiment of the present invention comprises a method of reducing edema in the penumbra of the spinal cord injury in a subject comprising administering to the subject a compound effective to inhibit a $NC_{Ca\text{-}ATP}$ channel in a neuronal cell, a neuroglia cell, a neural endothelial cell or a combination thereof.

Yet further, another embodiment of the present invention comprises treating a subject at risk for a spinal cord injury comprising administering an effective amount of a compound to inhibit the $NC_{Ca\text{-}ATP}$ channel in a neuronal cell, a neuroglia cell, an endothelial cell or a combination thereof. Subjects at risk can include those subjects that are undergoing a surgical treatment and/or a radiation treatment. Other subjects at risk can include subjects having a spinal condition, for example, segmental deformities, cord compressions caused by any known type of disease or infection, for example, Cushing's syndrome or arthritic diseases of the spine.

Still further, another embodiment of the present invention comprises a method of diagnosing neuronal cell edema and/or cytotoxic damage in the spinal cord of a subject comprising: labeling an antagonist of SUR1; administering the labeled antagonist of SUR1 to the subject; measuring the levels of labeled antagonist of SUR1 in the spinal cord of the subject, wherein the presence of labeled antagonist of SUR1 in the spinal cord of the subject indicates neuronal cell edema and/or cytotoxic damage in the spinal cord. Labeled antagonist can include a compound labeled with a fluorescent marker and/or a radioactive marker. The compound may comprise an inhibitor of SUR1, an antibody of SUR1, and/or a nucleic acid molecule, etc.

Another embodiment comprises a method of determining the penumbra following spinal cord injury in a subject comprising: labeling an antagonist of SUR1; administering the labeled antagonist of SUR1 to the subject; visualizing the labeled antagonist of SUR1 in the spinal cord of the subject, wherein the presence of labeled antagonist of SUR1 indicates the penumbra following a spinal cord injury in the subject.

In certain embodiments, determining the penumbra indicates the position of neuronal damage and/or monitors disease progression.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 5A was developed using antibodies directed against estrogen receptors (ER), demonstrating that both ERα and ERβ are expressed in astrocytes from both genders. Western blots showed that SUR1 is also expressed by cells from both genders, with pancreatic tissue used as control (FIG. 5B).

FIGS. 14A and 14B show images of frozen sections of spinal cord 24 hr after contusion injury for a rat treated with saline (FIG. 14A) and a rat treated with glibenclamide (FIG. 14B); note the smaller hemorrhage and preservation of contralateral structures with glibenclamide treatment. FIG. 14C shows test tubes containing homogenates of spinal cord 24 hr after contusion injury, for 2 rats treated with saline (left) and 2 rats treated with glibenclamide (right); note the difference in color, reflecting an apparent reduction in hemoglobin concentration with glibenclamide treatment.

FIGS. 16A and 16B show epifluorescence images of spinal cord sections 24 hr after contusion injury, immunolabeled for glial fibrillary acidic protein (GFAP), in a rat treated with saline (FIG. 16A) and a rat treated with glibenclamide (FIG. 16B). FIGS. 16C and 16D show images of spinal cord sections 24 hr after contusion injury, stained for myelin using eriochrome cyanine-R, in a rat treated with saline (FIG. 16C) and a rat treated with glibenclamide (FIG. 16D). Note the smaller lesions and sparing of contralateral structures with glibenclamide.

DETAILED DESCRIPTION OF THE INVENTION

I. Definitions

Figure 1:
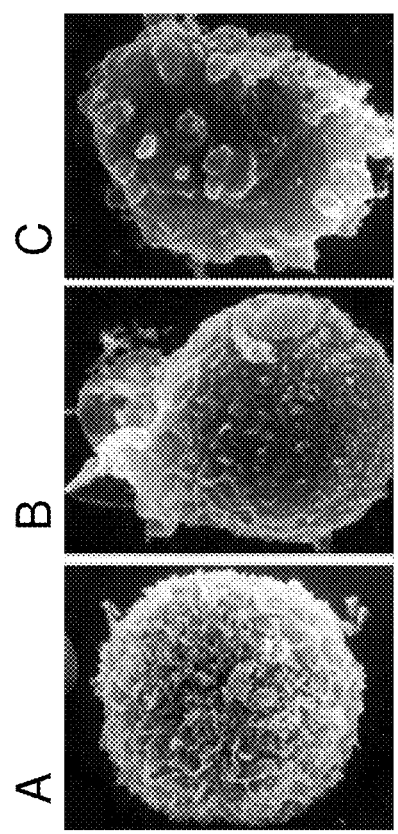
FIGS. 1A-1C show scanning electron micrographs showing appearance of freshly isolated reactive astrocyte (FIG. 1A) and blebbing 5 min (FIG. 1B) and 25 min (FIG. 1C) after exposure to 1 mM Na azide. Separate labeling showed that cells were GFAP-positive.

Unless defined otherwise, technical and scientific terms used herein have the same meaning as commonly understood by one of ordinary skill in the art to which this invention belongs. For purposes of the present invention, the following terms are defined below.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternative are mutually exclusive, although the disclosure supports a definition that refers to only alternatives and "and/or."

As used herein, the term "antagonist" refers to a biological or chemical agent that acts within the body to reduce the physiological activity of another chemical or biological substance. The term antagonist includes, but is not limited small molecules, chemicals, proteins, peptides, nucleic acid molecules, etc. In the present invention, the antagonist blocks, inhibits, reduces and/or decreases the activity of a $NC_{Ca\text{-}ATP}$ channel of a neuronal cell, a neuroglia cell or a neural endothelial cell (e.g., capillary endothelial cells). In the present invention, the antagonist combines, binds, associates with a $NC_{Ca\text{-}ATP}$ channel of neuronal cell, a neuroglia cell or a neural endothelial cell (e.g., capillary endothelial cells), such that the $NC_{Ca\text{-}ATP}$ channel is closed (deactivated, partially blocked, blocked, or inhibited), meaning reduced biological activity with respect to the biological activity in the diseased state. In certain embodiments, the antagonist combines, binds and/or associates with a regulatory subunit of the $NC_{Ca\text{-}ATP}$ channel, particularly a SUR1. Alternatively, the antagonist combines, binds, and/or associates with a pore-forming subunit of the $NC_{Ca\text{-}ATP}$ channel, such that the $NC_{Ca\text{-}ATP}$ channel is closed (deactivated and/or inhibited). The terms antagonist or inhibitor can be used interchangeably.

As used herein, the term "depolarization" refers to an increase in the permeability of the cell membrane to sodium ions wherein the electrical potential difference across the cell membrane is reduced or eliminated.

As used herein, the terms "effective amount" or "therapeutically effective amount" are interchangeable and refer to an amount that results in an improvement or remediation of the symptoms of the disease or condition. Those of skill in the art understand that the effective amount may improve the patient's or subject's condition, but may not be a complete cure of the disease and/or condition.

As used herein, the term "endothelium" refers a layer of cells that line the inside surfaces of body cavities, blood vessels, and lymph vessels or that form capillaries.

As used herein, the term "endothelial cell" refers to a cell of the endothelium or a cell that lines the surfaces of body cavities, for example, blood or lymph vessels or capillaries. In certain embodiments, the term endothelial cell refers to a neural endothelial cell or an endothelial cell that is part of the nervous system, for example the central nervous system, i.e., the spinal cord.

As used herein, the term "hemorrhagic conversion" refers to the pathological sequence that takes place in capillaries after ischemia. One of skill in the art is aware that hemorrhagic conversion is due to catastrophic failure of capillaries, during which all constituents of blood extravasate into the surrounding tissues. In accordance with Starling's law, understanding these phases requires that 2 things be identified: (i) the driving force that "pushes" things into tissue; and (ii) the permeability pore that allows passage of these things into tissue.

As used herein, the term "inhibit" refers to the ability of the compound to block, partially block, interfere, decrease, reduce or deactivate the $NC_{Ca-ATP}$ channel. Thus, one of skill in the art understands that the term inhibit encompasses a complete and/or partial loss of activity of the $NC_{Ca-ATP}$ channel as indicated by the reduction in cell depolarization, reduction in sodium ion influx or any other monovalent ion influx, reduction in an influx of water, reduction in extravasation of blood, reduction in cell death, as well as an improvement.

As used herein, the term "lesion" refers to any pathological or traumatic discontinuity of tissue or loss of function of a part thereof. For example, lesions includes any injury associated with the spinal cord, for example, but not limited to contusions, compression injuries, etc.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

As used herein, the term "neuronal cell" refers to a cell that is a morphologic and functional unit of the nervous system. The cell comprises a nerve cell body, the dendrites, and the axon. The terms neuron, nerve cell, neuronal, neurone, and neurocyte can be used interchangeably. Neuronal cell types can include, but are not limited to a typical nerve cell body showing internal structure, a horizontal cell (of Cajal) from cerebral cortex; Martinottic cell, bipolar cell, unipolar cell, Pukinje cell, and a pyramidal cell of motor area of cerebral cortex.

As used herein, the term "neural" refers to anything associated with the nervous system.

As used herein, the terms "neuroglia" or "neuroglial cell" refers to a cell that is a non-neuronal cellular element of the nervous system. The terms neuroglia, neurogliacyte, and neuroglial cell can be used interchangeably. Neuroglial cells can include, but are not limited to ependymal cells, astrocytes, oligodendrocytes, or microglia.

As used herein, the term "reduces" refers to a decrease in cell death, inflammatory response, hemorrhagic conversion, extravasation of blood, etc as compared to no treatment with the compound of the present invention. Thus, one of skill in the art is able to determine the scope of the reduction of any of the symptoms and/or conditions associated with a spinal cord injury in which the subject has received the treatment of the present invention compared to no treatment and/or what would otherwise have occurred without intervention.

The term "preventing" as used herein refers to minimizing, reducing or suppressing the risk of developing a disease state or parameters relating to the disease state or progression or other abnormal or deleterious conditions.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment, all of which are interchangeable. Thus, one of skill in the art is aware that spinal tissue includes all the neuronal cells, as well as any of the neuroglia cells associated therewith. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted.

The term "subject" as used herein, is taken to mean any mammalian subject to which the composition is administered according to the methods described herein. A skilled artisan realizes that a mammalian subject, includes, but is not limited to humans, monkeys, horses, pigs, cows, dogs, cats, rats and mice. In a specific embodiment, the methods of the present invention are employed to treat a human subject. In further embodiments, the subject is at risk of developing a spinal cord injury. Thus, the subject may or may not be cognizant of their disease state or potential disease state and may or may not be aware that they are need of treatment (therapeutic treatment or prophylactic treatment).

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

II. The Present Invention

The present invention is directed to therapeutic compositions and methods of using the same. In one embodiment, the therapeutic composition is an antagonist of a $NC_{Ca-ATP}$ channel of a neuronal cell, a neuroglial cell, or a neural endothelial cell.

In certain embodiments, the therapeutic compound of the present invention comprises an antagonist of a $NC_{Ca-ATP}$ channel of a neuronal cell, a neuroglia cell or an endothelial cell. Antagonists are contemplated for use in treating adverse conditions associated with cytotoxic and ionic edema of the central nervous system. Such conditions include trauma, spinal cord injury, namely secondary neuronal injury, for example, but not limited to hemorrhagic conversion, immune system reactions, oxidative damage, calcium and excitotoxicity, necrosis and apoptosis, and/or axon damage. The protection via inhibition of the $NC_{Ca-ATP}$ channel is associated with a reduction in edema, reduction in the generation of reactive oxidative species, reduction in inciting inflammation, and/or reduction in hemorrhagic conversion.

In one aspect, the $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux through the channel is reduced, ceased, decreased and/or stopped. The antagonist may have a reversible or an irreversible activity with respect to the activity of the $NC_{Ca-ATP}$ channel of the neuronal cell, neuroglial cell, endothelial cell or a combination thereof. The antagonist may prevent or lessen the depolarization of the cells thereby lessening cell swelling due to osmotic changes that can result from $Na^+$ influx and depolarization of the cells. Thus, inhibition of the $NC_{Ca-ATP}$ channel can reduce cytotoxic edema and death of cells, for example, necrotic death of cells.

In a preferred embodiment, the present invention provides a method of reducing spinal cord injury in a patient comprising administering an antagonist of a $NC_{Ca-ATP}$ channel of a neuronal cell, a neuroglia cell, or an endothelial cell, wherein the antagonist binds the channel. The binding of the $NC_{Ca-ATP}$ channel blocks the influx of $Na^+$ and water into the astrocyte, neuronal cell and endothelial cell, thereby reducing swelling at or around the injury. More particularly, the antagonist reduces the secondary injury from the initial spinal cord injury, for example, reduces the progression of a pathological involvement of the capillaries, i.e., hemorrhagic conversion, reduces immune system reactions, reduces oxidative damage, reduces calcium and excitotoxicity, reduces necrosis and cell death, and/or reduces axon damage.

III. $NC_{Ca-ATP}$ Channel

The invention is based, in part, on the discovery of a specific channel, the $NC_{Ca-ATP}$ channel, defined as a channel on astrocytes in US Application Publication No. 20030215889, which is incorporated herein by reference in its entirety. More specifically, the present invention has further defined that this channel is not only expressed on astrocytes, it is expressed on neural cells, neuroglial cells, and/or neural endothelial cells after central nervous system trauma, for example, a spinal cord contusion, or other secondary neuronal injuries relating to these events.

The $NC_{Ca-ATP}$ channel is activated by calcium ions ($Ca^{2+}$) and is sensitive to ATP. Thus, this channel is a non-selective cation channel activated by intracellular $Ca^{2+}$ and blocked by intracellular ATP. When opened by depletion of intracellular ATP, this channel is responsible for complete depolarization due to massive $Na^+$ influx, which creates an electrical gradient for $Cl^-$ and an osmotic gradient for $H_2O$, resulting in cytotoxic edema and cell death. When the channel is blocked or inhibited, massive $Na^+$ does not occur thereby preventing cytotoxic edema.

Certain functional characteristics distinguishes the $NC_{Ca-ATP}$ channel from other known ion channels. These characteristics can include, but are not limited to 1) it is a non-selective cation channels that readily allows passage of $Na^+$, $K^+$ and other monovalent cations; 2) it is activated by a decrease in intracellular ATP in the presence of intracellular $Ca^{2+}$; 3) it is regulated by sulfonylurea receptor type 1 (SUR1), which heretofore had been considered to be associated exclusively with $K_{ATP}$ channels such as those found in pancreatic β cells.

More specifically, the $NC_{Ca-ATP}$ channel of the present invention has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca-ATP}$ channel is also inhibited by cytoplasmic ATP in a physiological concentration range, where the concentration range is from $10^{-1}$ to 10 M. The $NC_{Ca-ATP}$ channel is also permeable to the following cations; $K^+$, $Cs^+$, $Li^+$, $Na^+$; to the extent that the permeability ratio between any two of the cations is greater than 0.5 and less than 2.

IV. Inhibitors of the $NC_{Ca-ATP}$ Channel

The present invention comprises inhibitors of the channel, for example an antagonist of the channel. Examples of antagonists of the present invention may encompass antagonists identified in US Application Publication No. 20030215889, which is incorporated herein by reference in its entirety. One of skill in the art is aware that the $NC_{Ca-ATP}$ channel is comprised to two subunits, the regulatory subunit, SUR1, and the pore forming subunit. One of skill in the art is aware that the nucleic acid sequences and amino acid sequences for SUR1 are readily available in GenBank, for example, GenBank accession L40624 (GI:1311533) and AAA99237 (GI:1311534), each of which is incorporated herein by reference in its entirety.

A. Inhibitors of SUR1

In certain embodiments, antagonists to sulfonylurea receptor-1 (SUR1) are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen-related compounds (estradiol, estrone, estriol, genistein, non-steroidal estrogen (e.g., diethystilbestrol), phytoestrogen (e.g., coumestrol), zearalenone, etc.) and combinations thereof. In a preferred embodiment of the invention the SUR1 antagonists is selected from the group consisting of glibenclamide and tolbutamide. Yet further, another antagonist can be MgADP. Other antagonist include blockers of $K_{ATP}$ channels, for example, but not limited to tolbutamide, glyburide (1[p-2[5-chloro-O-anisamido) ethyl]phenyl]sulfonyl]-3-cyclohexyl-3-urea); chlopropamide (1-[[(p-chlorophenyl)sulfonyl]-3-propylurea; glipizide (1-cyclohexyl-3[[p-[2(5-methylpyrazine carboxamido) ethyl]phenyl]sulfonyl]urea); or tolazamide(benzenesulfonamide-N-[[(hexahydro-1H-azepin-1yl)amino]carbonyl]-4-methyl).

B. Inhibitors of SUR1 Transcription and/or Translation

In certain embodiments, the inhibitor can be a compound (protein, nucleic acid, siRNA, etc.) that modulates transcription and/or translation of SUR1 (regulatory subunit) and/or the molecular entities that comprise the pore-forming subunit.

1. Transcription Factors

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

More specifically, transcription factors such as Sp1 and HIF1α can be used to modulate expression of SUR1. Those of skill in the art recognize that Sp1 and HIF1α can regulate SUR1 expression. Thus, one could prevent expression/activation of Sp1 that is normally induced by ischemia/hypoxia and/or hyperglycemia, that would in turn prevent expression of SUR1 (Chae Y M et al., 2004, incorporated herein by reference). Thus, inhibitors or molecules that prevent binding of Sp1 and/or HIF1 are contemplated in the present invention. Other such inhibitors of Sp1 can include, but are not limited to mithramycin.

Thus, it is contemplated that a candidate substance or SUR1 inhibitor may be a DNA-binding protein or transcription factor or a molecule or compound that inhibits or interferes with the activity or binding of a transcription factor, such as Sp1 or HIF1. It is proposed that the SUR1 inhibitor may bind to regulatory elements located within genes to alter transcription of the gene or may prevent the binding of DNA-binding proteins or transcription factors, such as Sp1 or HIF1. Also contemplated in the present invention is the interaction of a putative SUR1 inhibitor with another compound, e.g., a protein, to form a complex, which interacts with the DNA to alter transcription, such as prevents or reduces transcription. It will be understood that the compound that interacts with the putative SUR1 inhibitor may one or more than one compound.

2. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1.

a. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

b. RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SUR1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.,) and CLUSTAL (Higgins et al., 1992; Thompson, et al., 1994).

Thus, siRNA contains a nucleotide sequence that is essentially identical to at least a portion of the target gene, for example, SUR1, or any other molecular entity associated with the $NC_{Ca-ATP}$ channel such as the pore-forming subunit. One of skill in the art is aware that the nucleic acid sequences for SUR1 are readily available in GenBank, for example, GenBank accession L40624 (GI:1311533), which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

c. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in SUR1 targeted ribozymes is simply a matter of preparing and testing a given sequence, and is a routinely practiced screening method known to those of skill in the art.

C. Methods of Screening for Inhibitors

Further embodiments of the present invention can include methods for identifying inhibitors of the $NC_{Ca-ATP}$ channel, for example, antagonists, that modify the activity and/or expression. These assays may comprise random screening of large libraries of candidate substances; alternatively, the assays may be used to focus on particular classes of compounds selected with an eye towards structural attributes that are believed to make them more likely to modulate the function or activity or expression of the $NC_{Ca-ATP}$ channel.

By function, it is meant that one may assay for mRNA expression, protein expression, protein activity, or channel activity, more specifically, the ability of the modulator to inhibit or block the $NC_{Ca-ATP}$ channel. Thus, the compounds for screening in accordance with the invention include, but are not limited to natural or synthetic organic compounds, peptides, antibodies and fragments thereof, peptidomimetics, that bind to the $NC_{Ca-ATP}$ channel and either block the channel (e.g., antagonists).

With reference to screening of compounds that affect the $NC_{Ca-ATP}$ channel, libraries of known compounds can be screened, including natural products or synthetic chemicals, and biologically active materials, including proteins, for compounds which are inhibitors or activators. Preferably, such a compound is an $NC_{Ca-ATP}$ antagonist, which includes an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current through the channel.

Compounds may include, but are not limited to, small organic or inorganic molecules, compounds available in compound libraries, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof).

Other compounds which can be screened in accordance with the invention include but are not limited to small organic molecules that are able to cross the blood-brain barrier, gain entry into an appropriate neural cell and affect the expression of the $NC_{Ca-ATP}$ channel gene or some other gene involved in the $NC_{Ca-ATP}$ channel activity (e.g., by interacting with the regulatory region or transcription factors involved in gene expression); or such compounds that affects the activity of the $NC_{Ca-ATP}$ channel or the activity of some other intracellular factor involved in the $NC_{Ca-ATP}$ channel activity.

To identify, make, generate, provide, manufacture or obtain an inhibitor, one generally will determine the activity of the $NC_{Ca-ATP}$ channel in the presence, absence, or both of the candidate substance, wherein an inhibitor or antagonist is defined as any substance that down-regulates, reduces, inhibits, blocks or decreases the $NC_{Ca-ATP}$ channel expression or activity. For example, a method may generally comprise:

providing a candidate substance suspected inhibiting the $NC_{Ca-ATP}$ channel expression or activity in vitro or in vivo;

assessing the ability of the candidate substance to inhibit the $NC_{Ca-ATP}$ channel expression or activity in vitro or in vivo;

selecting an inhibitor; and manufacturing the inhibitor.

In certain embodiments, an alternative assessing step can be assessing the ability of the candidate substance to bind specifically to the $NC_{Ca-ATP}$ channel in vitro or in vivo;

In further embodiments, the $NC_{Ca-ATP}$ channel may be provided in a cell or a cell free system and the $NC_{Ca-ATP}$ channel may be contacted with the candidate substance. Next, the inhibitor is selected by assessing the effect of the candidate substance on the $NC_{Ca-ATP}$ channel activity or expression. Upon identification of the inhibitor, the method may further provide manufacturing of the inhibitor.

V. Treatment of Spinal Cord Injury

In other embodiments, the therapeutic compound of the present invention comprises an antagonist of a $NC_{cA-ATP}$ channel of a neuronal cell, a neuroglial cell, a neural endothelial cell or a combination thereof. Antagonists are contemplated for use in treating adverse conditions associated with a spinal cord injury. Such conditions include secondary damage associated with spinal cord injury, for example, but not limited to cell edema, cell death (e.g., necrotic cell death), inflammation, oxidative damage, axon damage, hemorrhagic conversion, etc. Antagonists protect the cells expressing the $NC_{Ca-ATP}$ channel, which is desirable for clinical treatment in which ionic or cytotoxic edema is formed, in which capillary integrity is lost. The protection via inhibition of the $NC_{Ca-ATP}$ channel is associated with a reduction in ionic and cytotoxic edema. Thus, the compound that inhibits the $NC_{Ca-ATP}$ channel is neuroprotective.

In one aspect, the $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux (ion and/or water) through the channel is reduced, ceased, decreased and/or stopped. The antagonist may have a reversible or an irreversible activity with respect to the activity of the $NC_{Ca-ATP}$ channel of the neuronal cell, neuroglial cell, a neural endothelial cell or a combination thereof. Thus, inhibition of the $NC_{Ca-ATP}$ channel can reduce cytotoxic edema and death of endothelial cells which are associated with formation of ionic edema and with hemorrhagic conversion.

Accordingly, the present invention is useful in the treatment or alleviation of inflammation associated with spinal cord injury. According to a specific embodiment of the present invention the administration of effective amounts of the active compound can block the channel, which if remained open leads to neuronal cell swelling and cell death, which lead to initiation of the inflammatory response. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen-related compounds and combinations thereof. In a preferred embodiment of the invention the SUR1 antagonists is selected from the group consisting of glibenclamide and tolbutamide. Another antagonist that can be used is MgADP. Still other therapeutic "strategies" for preventing neural cell swelling and cell death can be adopted including, but not limited to methods that maintain the neural cell in a polarized state and methods that prevent strong depolarization.

In further embodiments, inhibitors or antagonist of the $NC_{Ca-ATP}$ channel can be used to reduce or alleviate or abrogate hemorrhagic conversion and/or extravasated blood near or surrounding the injury site. With the administration of an antagonist of the $NC_{Ca-ATP}$ channel, endothelial cell depolarization is abrogated, slowed, reduced or inhibited due to the opening of the $NC_{Ca-ATP}$ channel. Thus, abrogation of cell depolarization results in abrogation or inhibition of $Na^+$ influx, which prevents a change in osmotic gradient thereby preventing an influx of water into the endothelial cell and stopping cell swelling, blebbing and cytotoxic edema. Thus, preventing or inhibiting or attenuating endothelial cell depolarization can prevent or reduce hemorrhagic conversion and/or extravasted blood near or surrounding the injury site.

Thus, the use of the antagonist or related-compounds thereof can reduce the mortality and/or morbidity of a subject suffering from a spinal cord injury and/or rescue the penumbra area or prevent damage in the penumbra area which comprises areas of tissue that are at risk of becoming irreversibly damaged.

Neuronal cells in which the antagonist of the $NC_{Ca-ATP}$ channel may be administered may include any cell that expresses SUR1, for example any neuronal cell, neuroglial cell or a neural endothelia cell.

Subjects that may be treated with the antagonist or related-compound thereof include those that are suffering from a spinal cord injury. Other subjects that may be treated with the antagonist of the present invention include those subjects that are at risk or predisposed to developing a spinal cord injury, such as a subject that is undergoing surgery of the spinal cord or radiation treatments to the spinal cord. In such cases, the subject may be treated with the antagonist or related-compound of the present invention prior to the actual treatment. Pretreatment can include administration of the antagonist and/or related-compound months (1, 2, 3, etc.), weeks (1, 2, 3, etc.), days (1, 2, 3, etc.), hours (1, 2, 3, 4, 5, 6, 7, 8, 9, 10, 11, 12), or minutes (15, 30, 60, 90, etc.) prior to the actual treatment or surgery or radiation treatment. Treatment of the antagonist and/or related-compound can continue during the treatment and/or surgery and after the treatment and/or surgery until the risk of developing a spinal cord injury in the subject is decreased, lessened or alleviated. Still further, other subjects at risk for a spinal cord injury can include those subjects that have segmental deformities and/or other spinal conditions or compression diseases, for example arthritis or Cushing's disease.

An effective amount of an antagonist of the $NC_{Ca-ATP}$ channel that may be administered to a cell includes a dose of about 0.0001 nM to about 2000 µM. More specifically, doses to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10

μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM and about 1500 μM to about 2000 μM. Of course, all of these amounts are exemplary, and any amount in-between these points is also expected to be of use in the invention.

The antagonist or related-compound thereof can be administered parenterally or alimentary. Parenteral administrations include, but are not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

The administration of the therapeutic compounds and/or the therapies of the present invention may include systemic, local and/or regional administrations, for example, topically (dermally, transdermally), via catheters, implantable pumps, etc. Alternatively, other routes of administration are also contemplated such as, for example, arterial perfusion, intracavitary, intraperitoneal, intrapleural, intraventricular and/or intrathecal. The skilled artisan is aware of determining the appropriate administration route using standard methods and procedures. Other routes of administration are discussed elsewhere in the specification and are incorporated herein by reference.

Treatment methods will involve treating an individual with an effective amount of a composition containing an antagonist of $NC_{Ca-ATP}$ channel or related-compound thereof. An effective amount is described, generally, as that amount sufficient to detectably and repeatedly to ameliorate, reduce, minimize or limit the extent of a disease or its symptoms. More specifically, it is envisioned that the treatment with the an antagonist of $NC_{Ca-ATP}$ channel or related-compounds thereof will inhibit cell depolarization, inhibit $Na^+$ influx, inhibit an osmotic gradient change, inhibit water influx into the cell, inhibit cytotoxic cell edema, decrease inflammation, inhibit or reduce oxidative damage or generation of reactive oxidative species, inhibit hemorrhagic conversion, decrease morbidity, and decrease mortality of the subject.

The effective amount of an antagonist of $NC_{Ca-ATP}$ channel or related-compounds thereof to be used are those amounts effective to produce beneficial results, particularly with respect to spinal cord injury treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of the $NC_{Ca-ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the effective amount of the antagonist or related-compound thereof can be the amount that is required to achieve the desired result: reduction inflammation, reduction in cell death, reduction in hemorrhagic conversion, reduction in extravasated blood, reduction the lesion size, reduction in the up-regulation of cGFAP, etc. This amount also is an amount that maintains a reasonable level of blood glucose in the patient, for example, the amount of the antagonist maintains a blood glucose level of at least 60 mmol/l, more preferably, the blood glucose level is maintain in the range of about 60 mmol/l to about 150 mmol/l. Thus, the amounts prevents the subject from becoming hypoglycemic. If glucose levels are not normal, then one of skill in the art would administer either insulin or glucose, depending upon if the patient is hypoglycemic or hyperglycemic.

Thus, in certain embodiments, the present invention comprises co-administration of an antagonist of the $NC_{Ca-ATP}$ channel with glucose or related carbohydrate to maintain appropriate levels of serum glucose. Appropriate levels of blood glucose are within the range of about 60 mmol/l to about 150 mmol/liter. Thus, glucose or a related carbohydrate is administered in combination to maintain the serum glucose within this range.

An effective amount of an antagonist of the $NC_{Ca-ATP}$ channel or related-compounds thereof as a treatment varies depending upon the host treated and the particular mode of administration. In one embodiment of the invention the dose range of the antagonist of the $NC_{Ca-ATP}$ channel or related-compounds thereof will be about 0.01 μg/kg body weight to about 20,000 μg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 μg/kg body weight to 20,000 μg/kg body weight, 0.02 μg/kg body weight to 15,000 μg/kg body weight, 0.03 μg/kg body weight to 10,000 μg/kg body weight, 0.04 μg/kg body weight to 5,000 μg/kg body weight, 0.05 μg/kg body weight to 2,500 μg/kg body weight, 0.06 μg/kg body weight to 1,000 μg/kg body weight, 0.07 μg/kg body weight to 500 μg/kg body weight, 0.08 μg/kg body weight to 400 μg/kg body weight, 0.09 μg/kg body weight to 200 μg/kg body weight or 0.1 μg/kg body weight to 100 μg/kg body weight. Further, those of skill will recognize that a variety of different dosage levels will be of use, for example, 0.0001 μg/kg, 0.0002 μg/kg, 0.0003 μg/kg, 0.0004 μg/kg, 0.005 μg/kg, 0.0007 μg/kg, 0.001 μg/kg, 0.1 μg/kg, 1.0 μg/kg, 1.5 μg/kg, 2.0 μg/kg, 5.0 μg/kg, 10.0 μg/kg, 15.0 μg/kg, 30.0 μg/kg, 50 μg/kg, 75 μg/kg, 80 μg/kg, 90 μg/kg, 100 μg/kg, 120 μg/kg, 140 μg/kg, 150 μg/kg, 160 μg/kg, 180 μg/kg, 200 μg/kg, 225 μg/kg, 250 μg/kg, 275 μg/kg, 300 μg/kg, 325 μg/kg, 350 μg/kg, 375 μg/kg, 400 μg/kg, 450 μg/kg, 500 μg/kg, 550 μg/kg, 600 μg/kg, 700 μg/kg, 750 μg/kg, 800 μg/kg, 900 μg/kg, 1 mg/kg, 5 mg/kg, 10 mg/kg, 12 mg/kg, 15 mg/kg, 20 mg/kg, and/or 30 mg/kg. Of course, all of these dosages are exemplary, and any dosage in-between these points is also expected to be of use in the invention. Any of the above dosage ranges or dosage levels may be employed for an antagonist of $NC_{Ca-ATP}$ channel or related-compounds thereof.

Administration of the therapeutic antagonist of $NC_{Ca-ATP}$ channel composition of the present invention to a patient or subject will follow general protocols for the administration of therapies taking into account the toxicity, if any, of the antagonist of the $NC_{Ca-ATP}$ channel. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the therapeutic composition (an antagonist of the $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

VI. Combination Treatments

In the context of the present invention, it is contemplated that an antagonist of the $NC_{Ca-ATP}$ channel or related-compounds thereof may be used in combination with an additional therapeutic agent to more effectively treat a spinal cord injury. In some embodiments, it is contemplated that a conventional therapy or agent, including but not limited to, a pharmacological therapeutic agent may be combined with the antagonist or related-compound of the present invention.

Pharmacological therapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agents that may be used in the present invention include an anti-inflammatory agent. Anti-inflammatory agents include, but are not limited to non-steroidal anti-inflammatory agents (e.g., naproxen, ibuprofen, celeocobix) and steroidal anti-inflammatory agents (e.g., glucocorticoids, dexamethasone, methylprednisolone).

Other agents that can be used in combination with the antagonist of the present invention can include, but are not limited to antioxidants, calcium blockers, drugs that control excitotoxicity, and drugs that enhance axon signaling, such as 4-aminopyridine.

Still further other agents that can be used in combination with the antagonist may also include agents designed to promote regeneration by using trophic factors, and growth-inhibiting substances.

Yet further, non-pharmacological interventions may also be used in combination with the antagonist of the present invention, such as transplantation, peripheral nerve grafts, hypothermia (cooling).

When an additional therapeutic agent, as long as the dose of the additional therapeutic agent does not exceed previously quoted toxicity levels, the effective amounts of the additional therapeutic agent may simply be defined as that amount effective to reduce edema or reduce secondary injury when administered to an animal in combination with $NC_{Ca-ATP}$ channel or related-compounds thereof. This may be easily determined by monitoring the animal or patient and measuring those physical and biochemical parameters of health and disease that are indicative of the success of a given treatment. Such methods are routine in animal testing and clinical practice.

To inhibit hemorrhagic conversion, reduce oxidative stress, reduce cell death, reduce cell swelling, etc., using the methods and compositions of the present invention, one would generally contact a cell with antagonist of $NC_{Ca-ATP}$ channel or related-compounds thereof in combination with an additional therapeutic agent, such as, an anti-inflammatory agent, etc. These compositions would be provided in a combined amount effective to inhibit hemorrhagic conversion, cell swelling, cell death, edema, etc. This process may involve contacting the cells with $NC_{Ca-ATP}$ channel or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes an antagonist of the $NC_{Ca-ATP}$ channel or derivatives thereof and the other includes the additional agent.

Alternatively, treatment with an antagonist of $NC_{Ca-ATP}$ channel or related-compounds thereof may precede or follow the additional agent treatment by intervals ranging from minutes to hours to weeks to months. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 1-24 hr of each other and, more preferably, within about 6-12 hr of each other.

VII. Formulations and Routes for Administration of Compounds

Pharmaceutical compositions of the present invention comprise an effective amount of one or more inhibitors of the $NC_{Ca-ATP}$ channel (antagonist) or related-compounds or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one modulators of $NC_{Ca-ATP}$ channel (antagonist and/or agonist) or related-compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inhibitors of the $NC_{CaATP}$ channel (antagonist) or related-compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The inhibitors of the $NC_{Ca-ATP}$ channel (i.e., antagonist) or related-compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include inhibitors of $NC_{CaATP}$ channel (antagonist) or related-compounds, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the inhibitors of $NC_{CaATP}$ channel (antagonist) or related-compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylatic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

A. Alimentary Compositions and Formulations

In preferred embodiments of the present invention, the antagonist or related-compounds of the $NC_{CaATP}$ channel are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft- shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629, 001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally- administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the antagonist or related-compounds of $NC_{CaATP}$ channel may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intraventricularly, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the antagonist or related-compounds of $NC_{CaATP}$ channel may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. Diagnostics

The antagonist or related-compound can be used for diagnosing, monitoring, or prognosis of spinal cord injury, for example monitoring the damage to neurons, or in monitoring neuronal cells in zones of edema, etc.

A. Genetic Diagnosis

One embodiment of the instant invention comprises a method for detecting expression of any portion of a $NC_{Ca\text{-}ATP}$ channel, for example, expression of the regulatory unit, SUR1, and/or expression of the pore-forming subunit. This may comprise determining the level of SUR1 expressed and/or the level of the pore-forming subunit expressed. It is understood by the present invention that the up-regulation or increased expression of the $NC_{Ca\text{-}ATP}$ channel relates to increased levels of SUR1, which correlates to increased neuronal damage, such as edema.

Firstly, a biological sample is obtained from a subject. The biological sample may be tissue or fluid. In certain embodiments, the biological sample includes cells from the spinal cord and/or endothelial cells or microvessels associated with the spinal cord or spinal tissue.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given subject with a statistically significant reference group of normal subjects and subjects that have been diagnosed with a spinal cord injury and or secondary injury associated therewith, etc.

Yet further, it is contemplated that chip-based DNA technologies such as those described by Hacia et al., (1996) and Shoemaker et al., (1996) can be used for diagnosis. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Other Types of Diagnosis

In order to increase the efficacy of molecules, for example, compounds and/or proteins and/or antibodies, as diagnostic agents, it is conventional to link or covalently bind or complex at least one desired molecule or moiety.

Certain examples of conjugates are those conjugates in which the molecule (for example, protein, antibody, and/or compound) is linked to a detectable label. "Detectable labels" are compounds and/or elements that can be detected due to their specific functional properties, and/or chemical characteristics, the use of which allows the antibody to which they are attached to be detected, and/or further quantified if desired.

Conjugates are generally preferred for use as diagnostic agents. Diagnostics generally fall within two classes, those for use in in vitro diagnostics, such as in a variety of immunoassays, and/or those for use in vivo diagnostic protocols, generally known as "molecule-directed imaging".

Many appropriate imaging agents are known in the art, as are methods for their attachment to molecules, for example, antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{11}$carbon, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Other types of conjugates contemplated in the present invention are those intended primarily for use in vitro, where the molecule is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

Immunologically-based detection methods for use in conjunction with Western blotting include enzymatically-, radiolabel-, or fluorescently-tagged secondary molecules/antibodies against the SUR1 or regulatory subunit of the NC$_{Ca-ATP}$ channel are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

In addition to the above imaging techniques, one of skill in the art is also aware that positron emission tomography, PET imaging or a PET scan, can also be used as a diagnostic examination. PET scans involve the acquisition of physiologic images based on the detection of radiation from the emission of positrons. Positrons are tiny particles emitted from a radioactive substance administered to the subject.

Thus, in certain embodiments of the present invention, the antagonist or related-compound thereof is enzymatically-, radiolabel-, or fluorescently-tagged, as described above and used to diagnose, monitor, and/or stage neuronal damage in the spinal cord and/or predict or stage secondary damage associated with the spinal cord injury. For example, the labeled antagonist or related-compound thereof may be used to determine or define the penumbra or the areas at risk for damage after a spinal cord injury.

IX. Diagnostic or Therapeutic Kits

Any of the compositions described herein may be comprised in a kit. In a non-limiting example, it is envisioned that a compound that selectively binds to or identifies SUR1 may be comprised in a diagnostic kit. Such compounds can be referred to as an "SUR1 marker", which may include, but are not limited to antibodies (monoclonal or polyclonal), SUR1 oligonucleotides, SUR1 polypeptides, small molecule or combinations thereof, antagonist, etc. It is envisioned that any of these SUR1 markers may be linked to a radioactive substance and/or a fluorescent marker and/or a enzymatic tag for quick determination. The kits may also comprise, in suitable container means a lipid, and/or an additional agent, for example a radioactive or enzymatic or florescent marker.

The kits may comprise a suitably aliquoted SUR1 marker, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. When there is more than one component in the kit, the kit also will generally contain a second, third or other additional container into which the additional components may be separately placed. However, various combinations of components may be comprised in a vial. The kits of the present invention also will typically include a means for containing the SUR1 marker, lipid, additional agent, and any other reagent containers in close confinement for commercial sale. Such containers may include injection or blow molded plastic containers into which the desired vials are retained.

Therapeutic kits of the present invention are kits comprising an antagonist or a related-compound thereof. Thus, the kit may comprise an SUR1 antagonist or related-compound thereof to block and/or inhibit the $NC_{Ca\text{-}ATP}$ channel. Such kits will generally contain, in suitable container means, a pharmaceutically acceptable formulation of SUR1 antagonist or related-compound thereof. The kit may have a single container means, and/or it may have distinct container means for each compound.

When the components of the kit are provided in one and/or more liquid solutions, the liquid solution is an aqueous solution, with a sterile aqueous solution being particularly preferred. The SUR1 antagonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO, polyethylene glycol (PEG) or ethanol that is used is no greater than 0.1% or (1 ml/1000 L).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the SUR1 antagonist or related-compounds thereof within the body of an animal. Such an instrument may be a syringe, pipette, forceps, and/or any such medically approved delivery vehicle.

In addition to the SUR1 antagonist or related-compounds thereof, the kits may also include a second active ingredient. Examples of the second active ingredient include substances to prevent hypoglycemia (e.g., glucose, D5W, glucagon, etc.), and steroids (e.g., methylprednisolone), etc. These second active ingredients may be combined in the same vial as the SUR1 antagonist or related-compounds thereof or they may be contained in a separate vial.

Still further, the kits of the present invention can also include glucose testing kits. Thus, the blood glucose of the patient is measured using the glucose testing kit, then the SUR1 antagonist or related-compounds thereof can be administered to the subject followed by measuring the blood glucose of the patient.

In addition to the above kits, the therapeutic kits of the present invention can be assembled such that an IV bag comprises a septum or chamber which can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Modulation of $NC_{Ca\text{-}ATP}$ Channel

When a cell is depolarized by a massive influx of $Na^+$, $H_2O$ is drawn into the cell due to the osmotic gradient. Influx of $H_2O$ causes cell blebbing, i.e., cytoxic edema. R1 astrocytes were examined for this phenomenon using scanning electron microscopy (SEM) and phase contrast microscopy. Freshly isolated cells examined with SEM showed a complex surface decorated with multiple fine processes (FIG. 1A). Shortly after exposure to Na azide, but well after depolarization is expected, the complex cell surface began to be replaced by surface blebs accompanied by smoothing out of the membrane (FIG. 1B). Later, the surface appearance was dominated by blebs, with complete loss of the delicate processes observed in controls (FIG. 1C).

Figure 2:
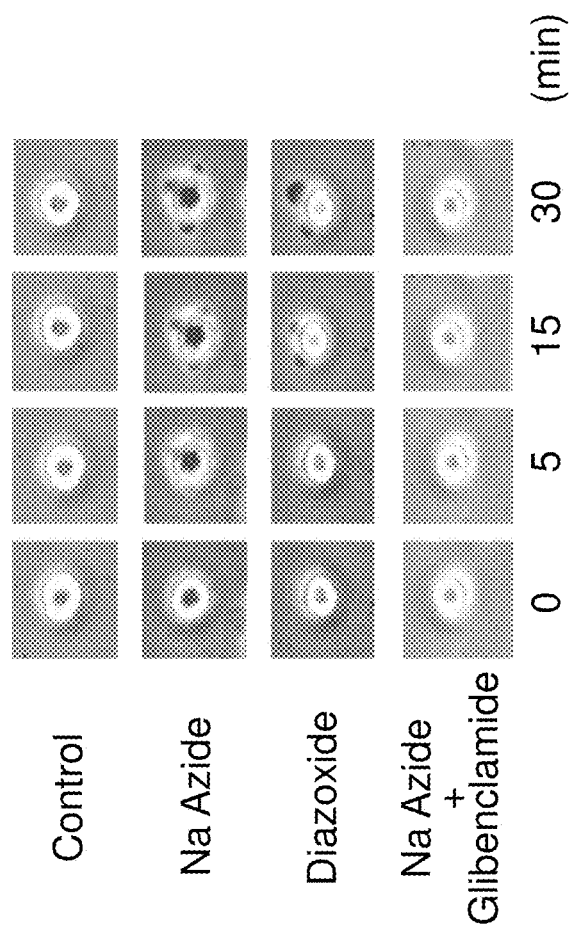
FIG. 2 shows a phase contrast micrographs showing appearance of freshly isolated reactive astrocytes under control conditions, and blebbing after exposure to 1 mM Na azide. Blebbing was reproduced by diazoxide alone, which opens the $NC_{Ca\text{-}ATP}$ channel, whereas Na-azide induced blebbing was blocked by glibenclamide, which blocks the channel. Separate labeling showed that cells were GFAP-positive.

Blebbing is reproduced in the absence of ATP depletion by simply opening the $NC_{Ca\text{-}ATP}$ channel with diazoxide (FIG. 2). Conversely, blebbing typically observed with Na azide-induced ATP depletion is completely prevented by glibenclamide (FIG. 2). Blebbing and cytotoxic edema presage necrotic cell death.

Example 2

Modulation by Estrogen

A characteristic feature of $K_{ATP}$ channels (Kir6.1, Kir6.2) is that channel affinity for ATP is modulated by the presence of the membrane lipid, phosphatidylinositol 4,5-bisphosphate ($PIP_2$). The open-state stability of $K_{ATP}$ channels is increased by application of $PIP_2$ to the cytoplasmic side of the membrane (Ashcroft, 1998; Baukrowitz et al., 1998; Rohacs et al., 1999). An increase in the open-state stability is manifested as an increase in the channel open probability in the absence of ATP, and in a corresponding decrease in sensitivity to inhibition by ATP (Enkvetchakul et al., 2000; Haruna et al., 2000; Koster et al., 1999; and Larsson et al., 2000).

Figure 3:
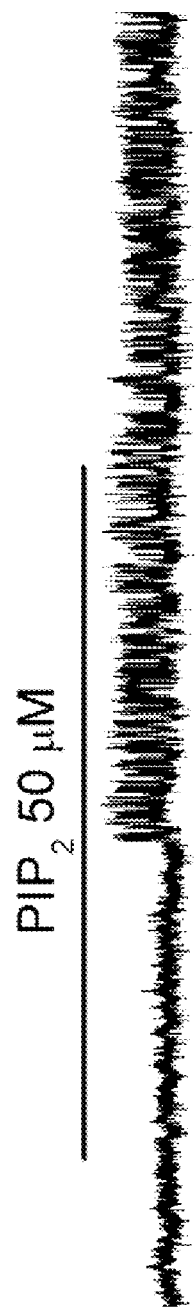
FIG. 3 shows that addition of exogenous phosphatidylinositol-4,5-bisphosphate (PIP$_2$) causes activation of the $NC_{CaATP}$ channel, despite the presence of ATP in the bath solution. Initially, channel activity was recorded in an inside-out patch of membrane from an R1 astrocyte, with a bath solution containing 1 µM $Ca^{2+}$ and 10 µM ATP, which was sufficient to block channel activity. Addition of 50 µM PIP$_2$ resulted in channel activation, reflecting an apparent decrease in affinity of the channel for ATP.

Given the numerous similarities between the $K_{ATP}$ channel and the $NC_{Ca\text{-}ATP}$ channel, the inventors postulated that ATP-sensitivity of the $NC_{Ca\text{-}ATP}$ channel would respond to $PIP_2$ in the same way. This was tested by studying $NC_{Ca\text{-}ATP}$ channels in inside out patches with $Cs^+$ as the charge carrier, and with 1 µM $Ca^{2+}$ and 10 µM ATP in the bath, with the latter expected to fully block the channel. Under these conditions, only the $NC_{Ca\text{-}ATP}$ channel was recorded in R1 astrocytes. When $PIP_2$ (50 µM) was added to the bath, channel activity became prominent (FIG. 3), as predicted by analogy to the effect of $PIP_2$ on $K_{ATP}$ channels. This channel activity was blocked by glibenclamide, confirming identity of the channel.

To determine if a receptor-mediated mechanism was involved in the modulation of $NC_{Ca\text{-}ATP}$ channel activity, a well known phospholipase C (PLC) was used to study if PLC activation would cause degradation and consumption of $PIP_2$ and thereby increase affinity for ATP, e.g., reduce channel opening. Estrogen is a well known PLC activator in brain as well as elsewhere (Beyer et al., 2002; Le Mellay et al., 1999; Qui et al., 2003). For this experiment, cell attached patches were studied to prevent alteration of intracellular signaling machinery. $NC_{Ca\text{-}ATP}$ channel activity was produced by exposure to Na azide to cause depletion of cellular ATP (FIG. 4, initial part of the record).

Figure 4:
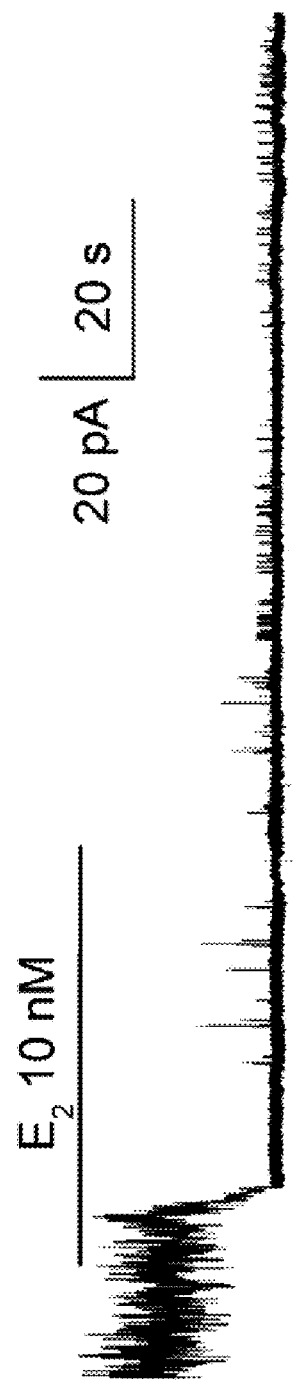
FIG. 4 shows that the $NC_{Ca\text{-}ATP}$ channel in an R1 astrocyte is inhibited by estrogen. The initial portion of the record shows brisk activity from a number of superimposed channels, recorded in a cell attached patch of membrane from an R1 astrocyte obtained from a female. Addition of 10 nM estrogen to the bath promptly resulted in strong inhibition of channel activity. The mechanism involved is believed to be related to estrogen receptor mediated activation of phospholipase C (PLC), resulting in depletion of PIP$_2$ from the membrane, and reflecting an apparent increase in affinity for ATP.

When estrogen (E2; 10 nM) was applied to the bath, activity due to the $NC_{Ca\text{-}ATP}$ channel was soon terminated (FIG. 4). This suggested that estrogen exerted regulatory control over the $NC_{Ca\text{-}ATP}$ channel, and suggested that an estrogen receptor capable of rapid (non-genomic) activation of signaling cascades was present on these cells.

Figure 5:
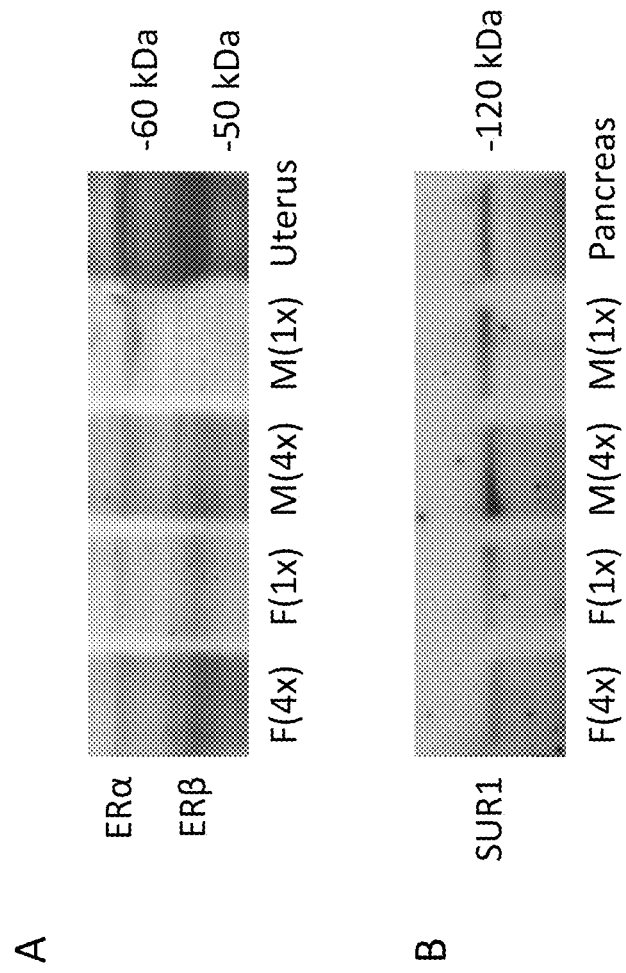
FIGS. 5A-5B show Western blots demonstrating that R1 astrocytes from both males and females express estrogen receptors and SUR1, a marker of the $NC_{Ca\text{-}ATP}$ channel. Cell lysates were obtained from gelatin sponge implants from males (M) and females (F) and studied at two dilutions (4× and 1×), with lysates from uterus used as controls.

Next, to determine whether estrogen receptors could be detected in R1 astrocytes from males and females, gelatin sponge implants were harvested 7 days after implantation in a group of 3 female rats (F) and another group of 3 male rats (M). Pooled protein from each group was analyzed at 2 dilutions (4x=50 µg total protein; 1x=12.5 µg total protein) by Western blotting, with protein from uterus being used as a control (FIG. 5A). Membranes were blotted with an antibody that recognized both α and β estrogen receptors. Both males and females showed prominent bands at the appropriate molecular weights for the α (66 kDa) and β (55 kDa) receptors (FIG. 5) (Hiroi et al., 1999). The same samples of protein from males and females were also used to confirm presence of SUR1, with protein from pancreas used as a positive control (FIG. 5B). Notably, estrogen receptors have previously been reported in astrocytes from males and females (Choi et al., 2001). In cerebral cortex, the β isoform is reportedly more abundant (Guo et al., 2001) as suggested by the Western blot.

Figure 6:
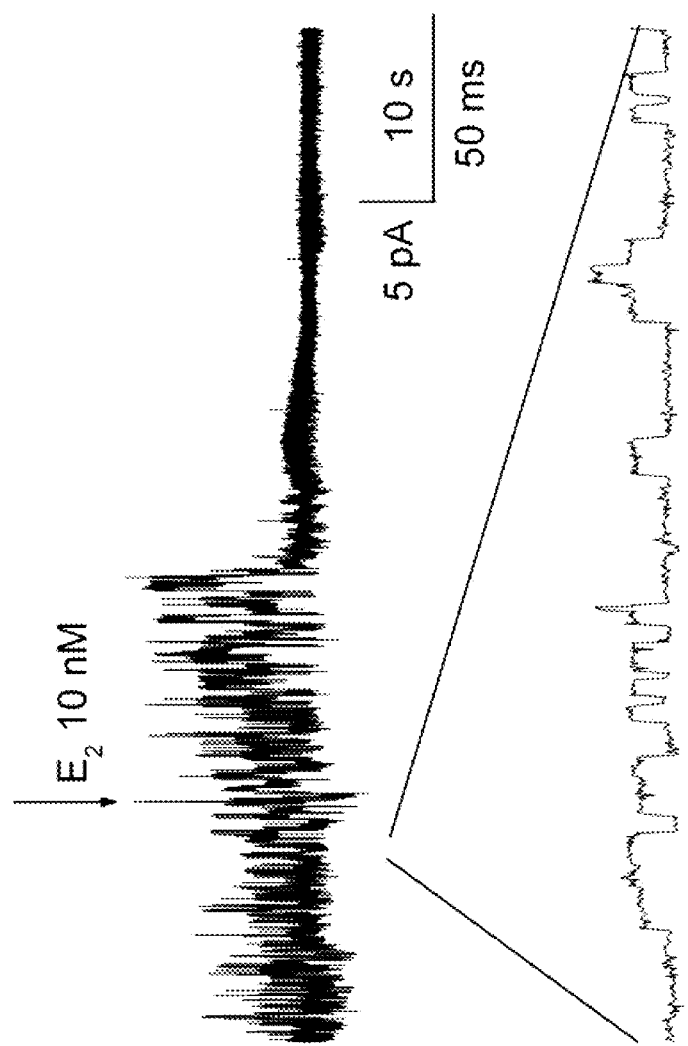
FIG. 6 shows that the $NC_{Ca\text{-}ATP}$ channel in an R1 astrocyte from a male is inhibited by estrogen. The initial portion of the record shows brisk activity from a number of superimposed channels, recorded in a cell attached patch of membrane from an R1 astrocyte obtained from a male. Addition of 10 nM estrogen to the bath promptly resulted in strong inhibition of channel activity.

Next, the electrophysiological experiment of FIG. 4 was repeated using R1 astrocytes harvested from male rats. As above, cell attached patches were studied in which $NC_{Ca\text{-}ATP}$ channel activity was activated by depletion of intracellular ATP following exposure to Na azide (FIG. 6A). Examination of the record at higher temporal resolution confirmed activity of a well defined channel of the appropriate conductance for the $NC_{Ca\text{-}ATP}$ channel (FIG. 6B). When estrogen was applied to the bath (FIG. 6, E2, 10 nM, arrow), activity due to the $NC_{Ca\text{-}ATP}$ channel was quickly terminated (FIG. 6). These data provided further evidence that estrogen exerted regulatory control over the $NC_{Ca\text{-}ATP}$ channel, and suggested, in addition, that this response was equally robust in R1 astrocytes from males and females.

By analogy to the effects of estrogen, other mechanisms that deplete $PIP_2$, including other receptor-mediated mechanism as well as more direct activators of PLC such as G-proteins etc., would be expected to have a similar inhibitory effect on activity of the $NC_{Ca\text{-}ATP}$ channel and thereby exert a protective effect.

Example 3

$NC_{Ca\text{-}ATP}$ Channel and Necrotic Death

Figure 7:
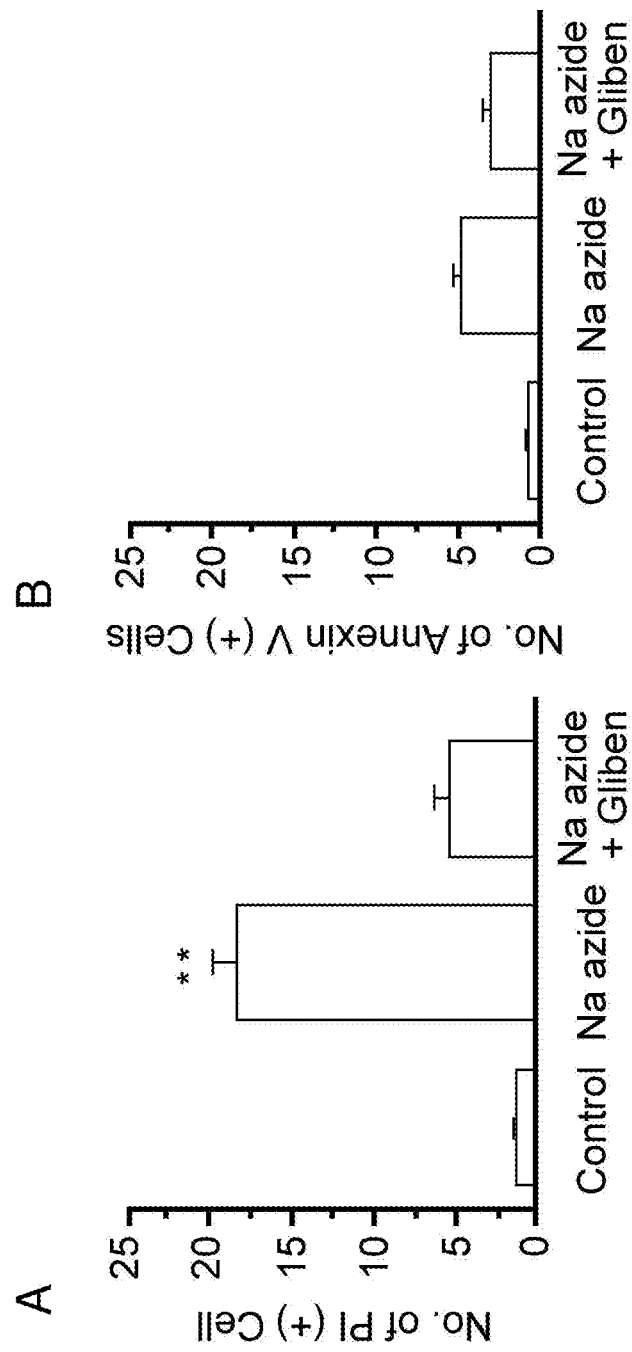
FIGS. 7A-7B shows Na azide-induced blebbing is followed by necrotic death of freshly isolated reactive astrocytes. Cell death was assessed using propidium iodide (PI) to identify necrotic death (FIG. 7A) and annexin V to identify apoptotic death (FIG. 7B). The significant rise in necrotic death induced by 1 mM Na azide was strongly attenuated by 1 µM glibenclamide (FIG. 7A). Apoptotic death was minimal after exposure to Na azide (FIG. 7B).

Applicants discovered a new mechanism of necrotic death of reactive astrocytes in brain injury and stroke that implicate an important role in spinal cord injury. Blebbing and cytotoxic edema presage necrotic cell death. Freshly isolated reactive astrocytes were labeled with propidium iodide, a marker of necrotic death, and for annexin V, a marker of apoptotic death. Cells exposed to Na azide showed a marked increase in necrotic but not apoptotic death (FIG. 7). However, when glibenclamide was present, Na azide-induced necrotic cell death was significantly reduced (FIG. 7). These in vitro data show the important role of the $NC_{Ca\text{-}ATP}$ channel in necrotic death of reactive astrocytes, and indicate antagonists of SUR1, such as glibenclamide, are useful in preventing cytotoxic edema and necrotic death in vivo.

Figure 8:
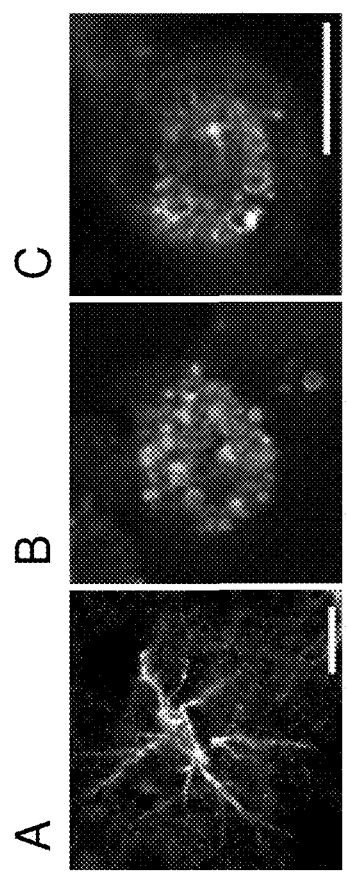
FIGS. 8A-8C shows immunofluorescence images of 1 cell in the penumbra (FIG. 8A) and 2 cells in the middle of a stroke in the brain (FIG. 8B, 8C), immunolabeled for SUR1; co-labeling with GFAP confirmed their identity as astrocytes; note "bleb-like" pattern of labeling.

The Applicants studied $NC_{Ca\text{-}ATP}$ channels in a rodent model of stroke. In the penumbra, SUR1 labeling was found in stellate-shaped cells (FIG. 8A) that were also GFAP-positive. In the middle of the stroke, stellate cells were absent, but SUR1 labeling was found in round cells exhibiting a bleb-like appearance (FIG. 8B,C) that were also GFAP-positive. The round cells with blebbing in situ resembled reactive astrocytes in vitro undergoing necrotic death after exposure to Na azide. The effect of glibenclamide vs. saline was examined, administered via subcutaneously-implanted osmotic mini-pump (300 µM at 0.5 µl/hr). In saline treated rats, 3-day mortality after stroke was 68%, whereas in glibenclamide-treated rats, 3-day mortality was reduced to 28% (n=20 in each group; $p<0.001$, by $\chi^2$). In separate animals, it was found that the stroke hemisphere in glibenclamide-treated rats contained only half as much excess water as in saline-treated rats (n=5 in each group; $p<0.01$, by t-test), confirming an important role of the $NC_{Ca\text{-}ATP}$ channel in edema formation.

The Applicants also studied SUR1 in a rodent model of trauma. The effect of direct infusion of drugs into the site of trauma using an implanted osmotic mini-pump was examined. The channel inhibitor, glibenclamide, was used to reduce death of reactive astrocytes, and the channel activator, diazoxide, to promote astrocyte death. Briefly, it was found that glibenclamide infusion reduced the overall injury response, stabilized the gliotic capsule around the foreign body implant, and minimized the inflammatory response compared to control.

Figure 9:
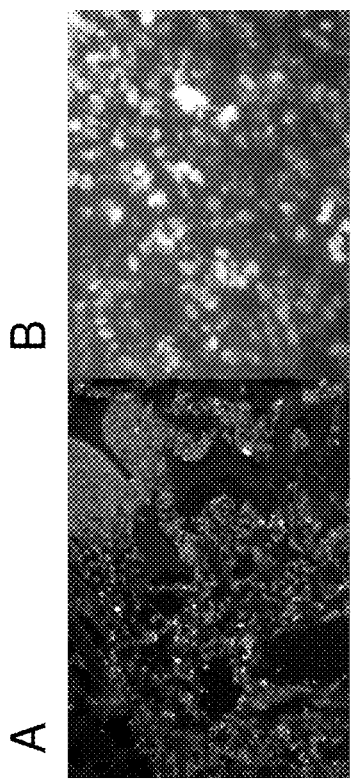
FIGS. 9A-9B show images of traumatic brain injury site after infusion of diazoxide to induce necrotic death of reactive astrocytes. Sections were labeled with the nuclear marker, DAPI, showing sheets of small cells (FIG. 9A), and immunolabeled with anti-MMP-8 antibody, to identify the cells as PMNs (FIG. 9B).

Conversely, diazoxide essentially destroyed the gliotic capsule and incited a huge inflammatory response, characterized by massive influx of PMNs (FIG. 9A, B). These data suggested that $NC_{Ca\text{-}ATP}$ channel plays a critical role in the injury response, and they strongly supported the hypothesis that inflammation was closely linked to activity of the $NC_{Ca\text{-}ATP}$ channel and necrotic death of reactive astrocytes.

Example 4

Expression of Functional $NC_{Ca\text{-}ATP}$ Channels in Spinal Cord Contusion

Figure 10:
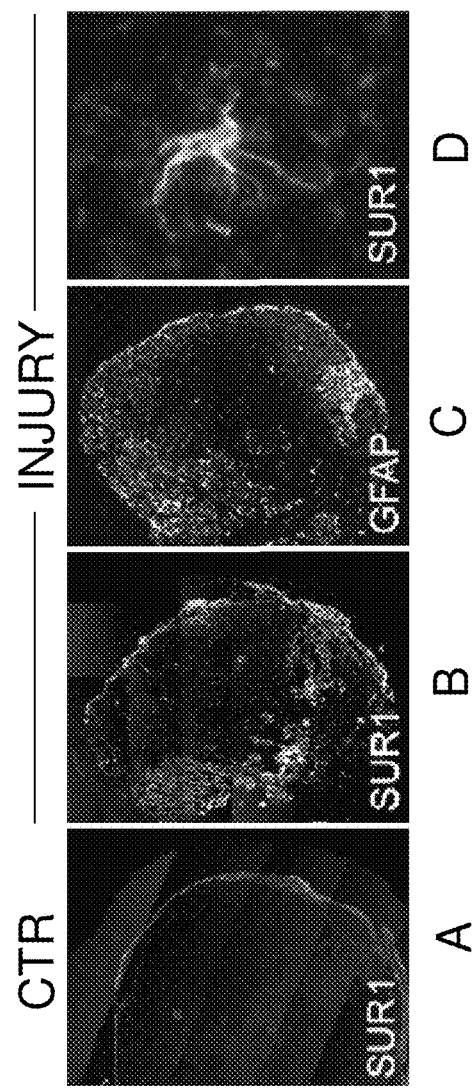
FIGS. 10A-10D show immunofluorescence (composite) images of spinal cord sections from control (FIG. 10A) and 24-hr after severe bilateral thoracic spinal cord crush injury (FIGS. 10B-10D), labeled for SUR1 (FIGS. 10A, 10B, 10D) or GFAP (FIG. 10C). At high magnification, individual SUR1-positive loci seen in (FIG. 10B) correspond to GFAP-positive stellate cells (FIG. 10D) consistent with reactive astrocytes.

SUR1 in a rodent model of spinal cord contusion was identified. Immunolabeled spinal cord sections showed a large increase in SUR1 expression in the region of injury (FIG. 10B), compared to control (FIG. 10A). SUR1 was co-localized with GFAP (FIG. 10C), confirming involvement of reactive astrocytes. Examination of cells at high power confirmed that SUR1-positive cells were stellate-shaped (FIG. 10D) GFAP-positive cells, consistent with the hypothesis that reactive astrocytes in spinal cord injury express the $NC_{Ca-ATP}$ channel.

Further characterization of reactive astrocytes is carried out by isolating reactive astrocytes from contused spinal cord 3-5 days after injury using fluorescence-assisted cell sorting (FACS). Freshly isolated cells are patch clamped to demonstrate channels with expected physiological and pharmacological properties. A spinal cord injury (SCI) model is used and includes use of the NYU-style impactor (Yu et al., 2001). Reactive astrocytes are isolated from enzymatically dispersed spinal cord tissue using anti-SUR1 antibody and FACS. Use of FACS for isolation of another subtype of reactive astrocyte in brain injury (Dalton et al., 2003). Patch clamp methods are used to measure single channel conductance, sensitivity to ATP, and sensitivity to glibenclamide and diazoxide, as described astrocytes isolated from brain injury (Chen et al., 2001; Chen and Simard, 2003).

Example 5

Block of SUR1 Prevents Delayed Hemorrhagic Conversion

The lesion in spinal cord contusion results not only from physical trauma to the tissues, but also from secondary damage that causes expansion of the original lesion and worsens neurological compromise. Mechanisms of secondary are generally attributed to development of ischemia, edema, release of excitatory amino acids, oxidative injury and inflammation. The Applicants discovered that hemorrhage also is a key component of this process of secondary injury. Hemorrhage expands after injury, because of progressive pathological involvement of capillaries, a phenomenon that is termed "hemorrhagic conversion".

Figure 11:
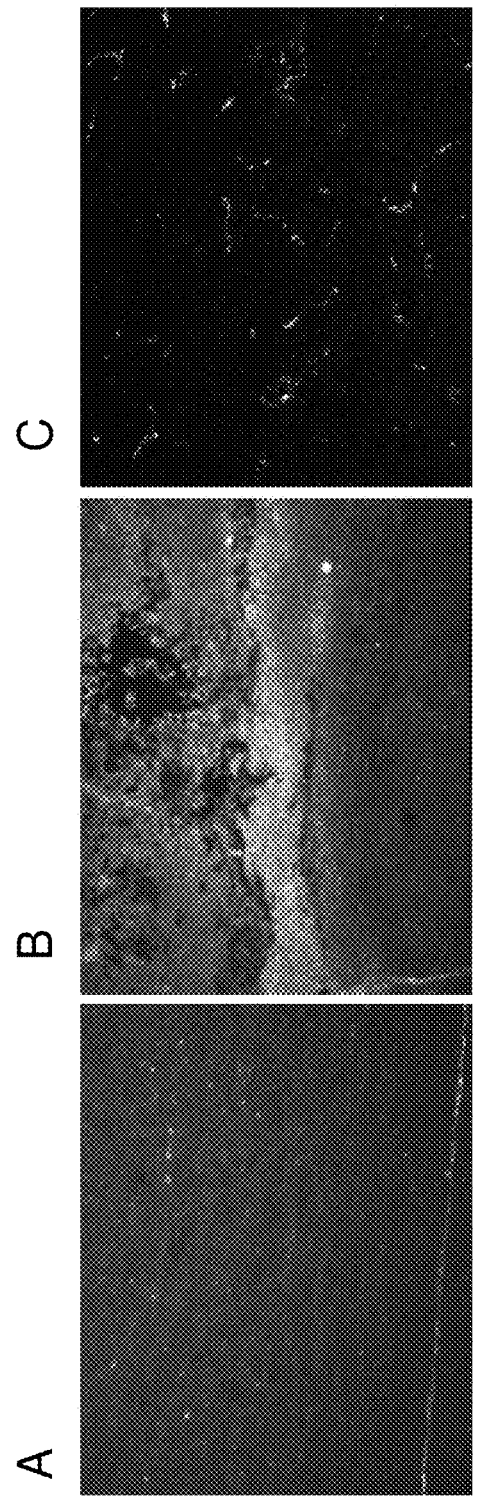
FIGS. 11A-11C shows SUR1 up-regulation in a cervical hemi-spinal cord contusion injury of moderate severity (SCI; same model as used in all subsequent illustrations). Epifluorescence images of spinal cord tissues immunolabeled for SUR1 from control region (FIG. 11A) and from region of contusion injury, shown at low power (FIG. 11B) and at high power (FIG. 11C). The high power view demonstrates that in this model, SUR1 expression at 24 hr occurs primarily in capillaries.
Figure 12:
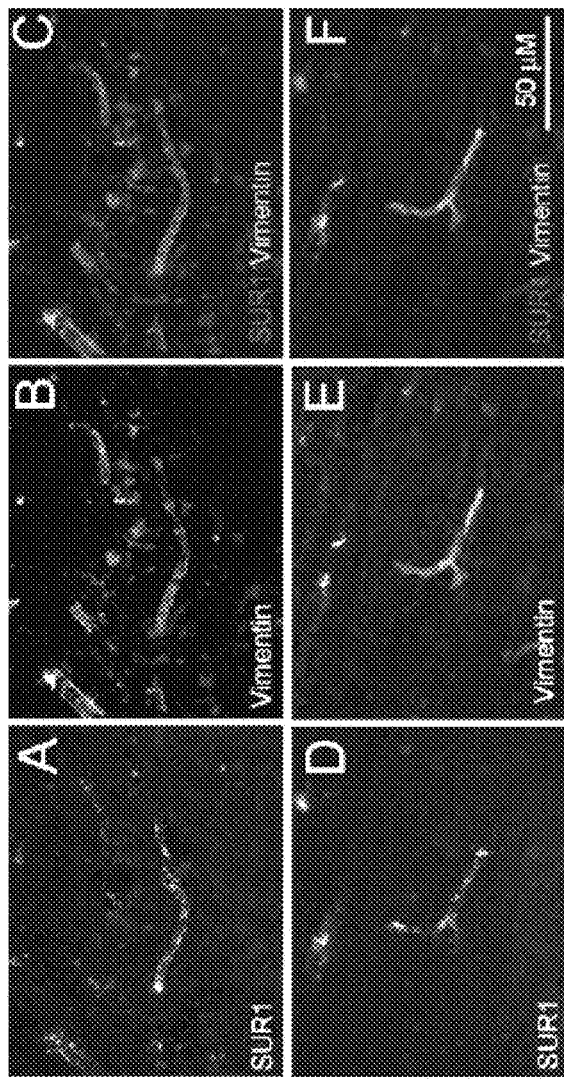
FIGS. 12A-12F show SUR1 and vimentin are up-regulated in capillaries in SCI. Epifluorescence images of spinal cord tissues from 2 rats immunolabeled for SUR1 (FIGS. 12A, 12D), immunolabeled for vimentin (FIGS. 12B, 12E), and coimmunolabeled for SUR1 and vimentin (FIGS. 12C, 12F) 24 hr after contusion injury; superimposed images are shown.

To study the role of the SUR1-regulated $NC_{Ca-ATP}$ channel in SCI, a hemi-cervical spinal cord contusion model was used. For this model, a 10 gm weight is dropped 2.5 cm onto the left half of the exposed dura at C4-5 in adult female Long-Evans rats. Histopathological study 24 hr after injury showed abundant up-regulation of SUR1 in capillaries surrounding the area of injury that was not present in controls (FIG. 11). In addition, capillaries in the injury site that showed up-regulation of SUR1 were also found to express vimentin (FIG. 12), an intermediate filament protein commonly associated with astrocytes, but that is also expressed by injured capillary endothelial cells in brain and spinal cord.

Figure 13:
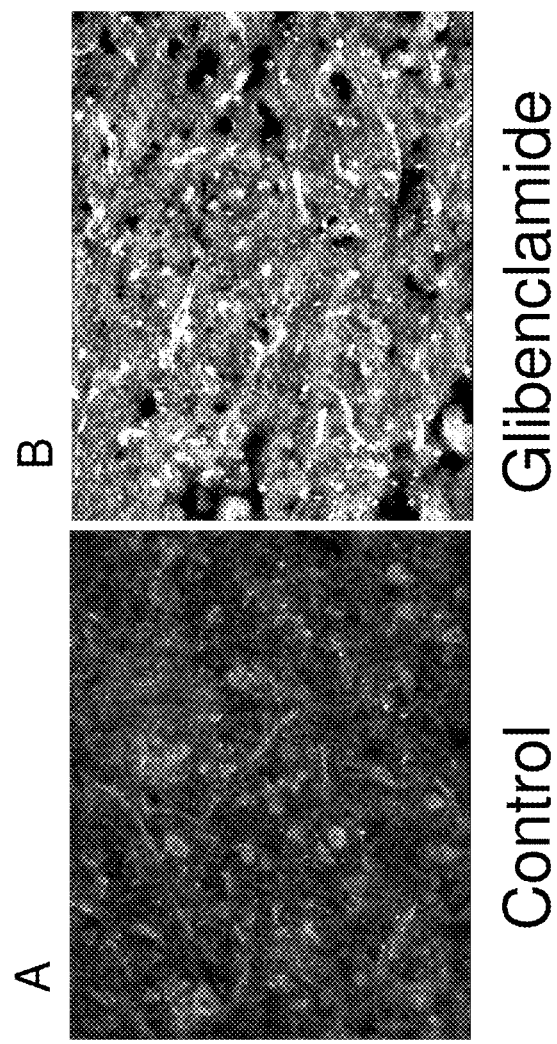
FIGS. 13A-B show up-regulation of the transcription factor, SP1, which is the principal transcription factor known to regulate expression of SUR1. Epifluorescence images of spinal cord tissues from 2 rats immunolabeled for SP1, a control uninjured spinal cord (FIG. 13A) and a spinal cord 24 hr after contusion injury (FIG. 13B).

To provide further molecular evidence for involvement of SUR1, tissues in spinal cord injury were also examined for the transcription factor, SP1, which is the principal transcription factor known to regulate expression of SUR1. Immunolabeling of tissues in the region of injury showed prominent up-regulation of SP1 (FIG. 13B), compared to control (FIG. 13A).

Figure 14:
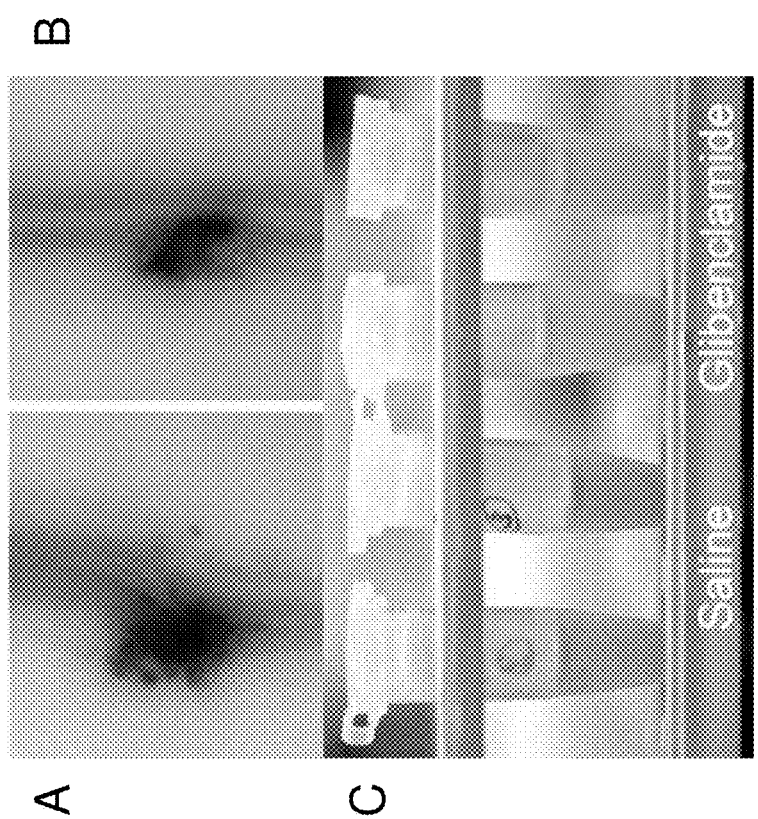
FIGS. 14A-14C show glibenclamide treatment reduces hemorrhagic conversion.
Figure 15:
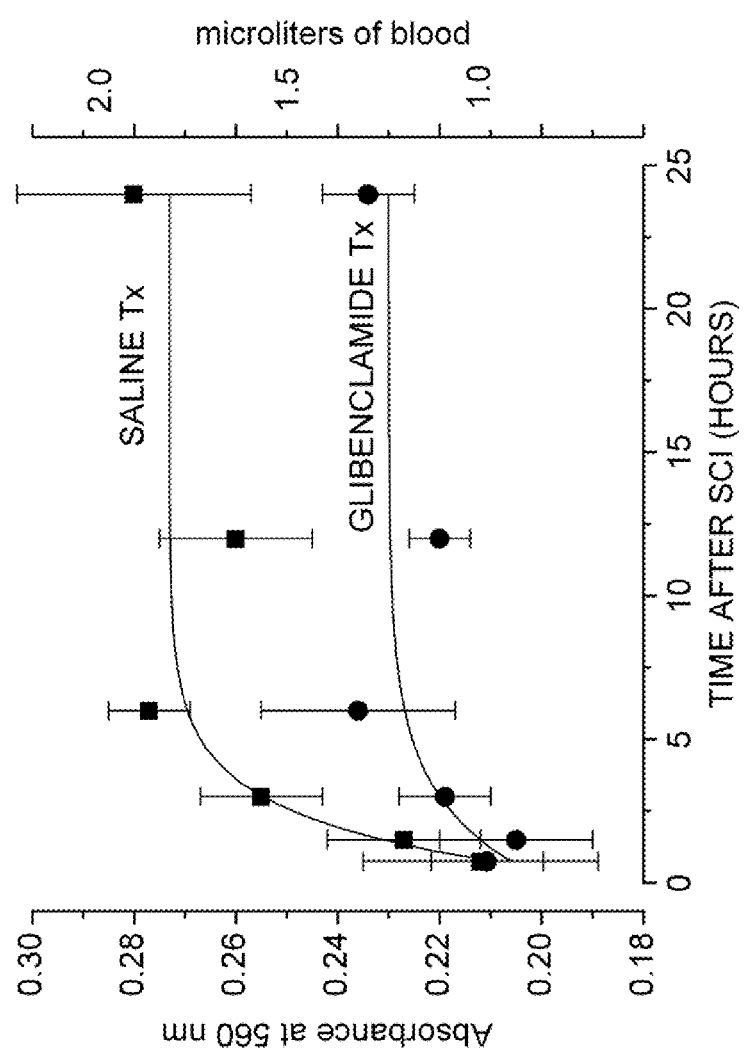
FIG. 15 shows the effect of glibenclamide treatment on the time course of hemorrhagic conversion after spinal cord injury (SCI). Extravasated blood in the region of injury was assessed at various times after SCI. At the time of sacrifice, intravascular blood was first removed by perfusion, then a 5 mm segment of spinal cord encompassing the contused area was excised, weighed and homogenized in a volume of distilled water 9× the mass of the tissue. The content of blood was quantified using Drabkin reagent (5 rats per group). Values were expressed as absorbance at 560 nm or as microliters of blood, assuming a hematocrit of 40%. In saline-treated animals, the amount of blood increased progressively with time following SCI, reaching a plateau 6 hours after injury (filled squares). In glibenclamide-treated animals, values at 45 min were similar to controls, but as time progressed after SCI, values increased significantly less than in controls (filled circles).

To assess the role of newly expressed SUR1 in SCI, 2 groups of animals were studied, one control- and one treatment-group, both of which underwent hemicervical spinal cord contusion plus post-injury implantation (blinded) of a miniosmotic pump that delivered subcutaneously either saline or the selective SUR1 blocker, low-dose glibenclamide (300 µM solution delivered at 0.5 µl/hr s.q.). Study 24 hr after injury showed that, compared to controls, glibenclamide-treated animals had significantly less blood in the contusion site (FIG. 14A,B). Also, homogenates of spinal cord tissue showed significantly less coloration from hemoglobin/hemosiderin (FIG. 14C). Quantitative study of hemoglobin concentration as a function of time after spinal cord contusion showed a progressive increase over the first 6 hours after injury in saline-treated animals that was significantly ameliorated by treatment with glibenclamide (FIG. 15)

Figure 16:
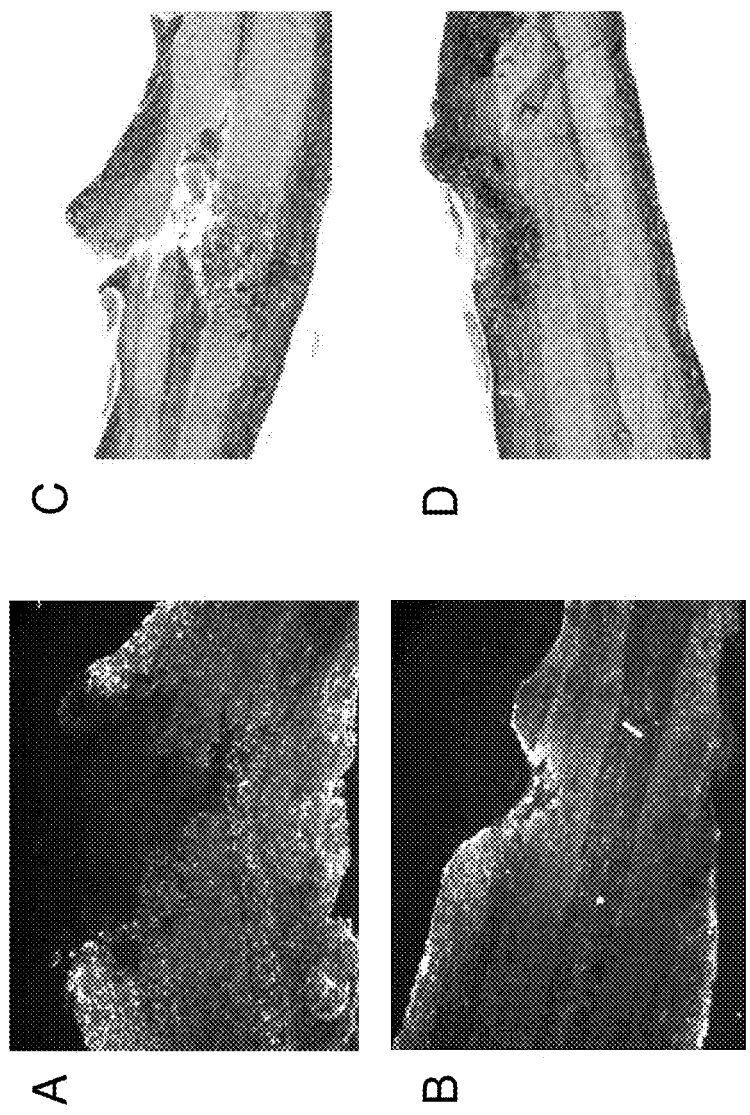
FIGS. 16A-16D show glibenclamide treatment reduces lesion size, GFAP expression, and preserves contralateral long tracks.

Next, the lesions in the two groups of animals were assessed using GFAP to label reactive astrocytes and eriochrome cyanine-R to label myelin. Study 24 hr after injury showed that, compared to controls, glibenclamide-treated animals had significantly smaller lesions, significantly reduced GFAP expression, and significantly better preservation of contralateral long tracts (FIG. 16).

Figure 17:
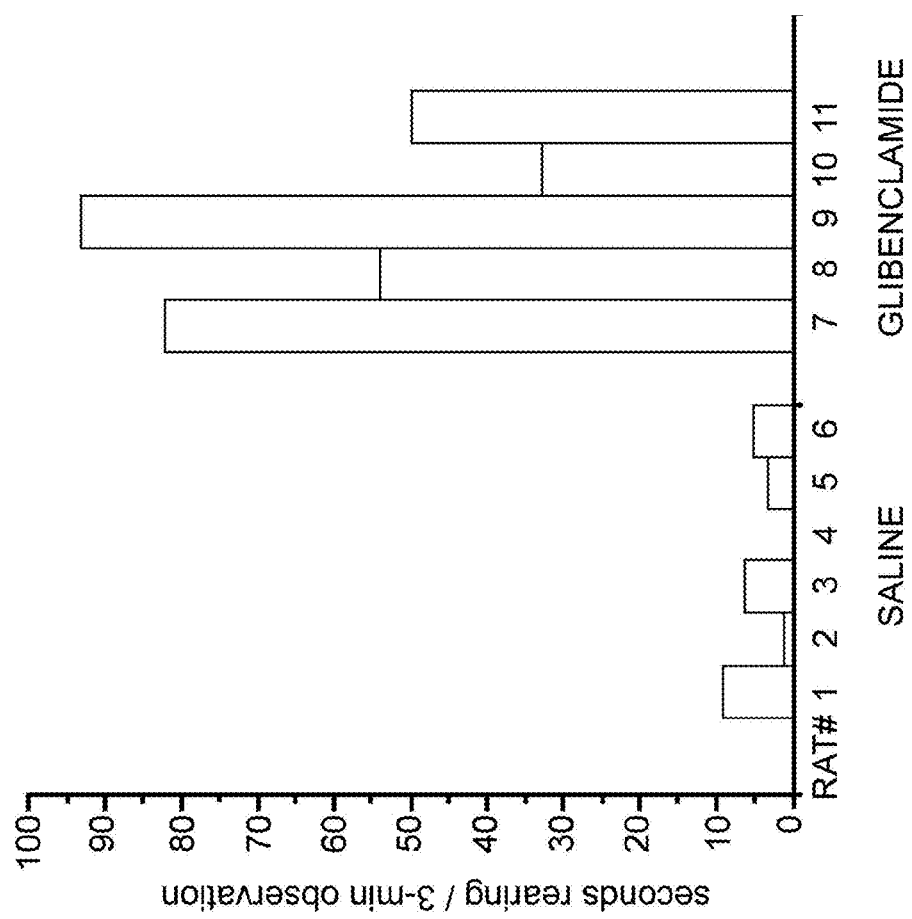
FIG. 17 shows glibenclamide treatment improves vertical exploration following SCI contusion. Bar graphs showing the number of seconds spent in vertical exploration (rearing) per 3-min period of observation, 24 hr after contusion injury, for 6 rats treated with saline, and for 5 rats treated with glibenclamide.

Yet further, behavioral assessments in the two groups of animals were performed. The animals were video-taped and vertical exploratory behavior was quantified in an environment that animals had not been previously exposed to. Study 24 hr after injury showed that, compared to controls, glibenclamide-treated animals exhibited significantly improved vertical exploratory behavior (FIG. 17).

Recognition of the phenomenon of delayed hemorrhagic conversion in spinal cord contusion provides an extraordinary opportunity to reduce secondary damage. As is widely known, blood is severely toxic to CNS tissues, and is responsible for formation of edema, generation of reactive oxidative species, and inciting inflammation. The concept of delayed hemorrhagic conversion is a novel concept in SCI, and discovery that glibenclamide can be used to ameliorate this condition provides an unprecedented opportunity to improve outcome by reducing secondary damage.

Example 6

Role of $NC_{Ca-ATP}$ Channels in Cytotoxic Edema and Necrotic Death of Astrocytes and Release of Biologically Active Molecules that Promote Tissue Inflammation Identification of candidate intracellular molecule(s) released by cell membrane lysis during necrotic cell death that play a role in initiating an inflammatory response in spinal cord injury is also contemplated in the present invention. Reactive astrocytes are isolated from contused spinal cord 3-5 days after injury using FACS. Using freshly isolated cells, the effect of Na azide (1 mM) vs. Na azide plus glibenclamide (1 µM) on necrotic vs. apoptotic cell death during the first 3 hr after poisoning is assessed by: performing morphological studies using phase contrast microscopy, scanning electron microscopy and transmission electron microscopy; labeling for propidium iodide vs. annexin V; and assessing DNA degradation using TUNEL labeling and DNA laddering.

Using freshly isolated cells, ELISAs are used to measure release of HSP-32 and HSP-70 following necrotic death of astrocytes induced by Na azide. Also, using the same experimental paradigm, we will assess the protective effect of glibenclamide on Na azide-induced release of HSP-32 and HSP-70. Standard FACS methods are used as well as scanning and transmission electron microscopy and phase contrast microscopy, which allows an individual cell to be followed sequentially during blebbing. Immunofluorescence is also used, as described herein.

Example 7

Ability of Antagonist of NC$_{Ca-ATP}$ Channel to Reduce Inflammatory Response in Spinal Cord Contusion in vivo Tissues are studied about 3 days after injury. In rats with spinal cord contusion treated with either saline or glibenclamide, the inflammatory response in situ is assessed using qualitative immunofluorescence labeling for activated microglia (OX-42), macrophages (MAC-387, Novus), PMNs (MMP-8, Chemicon) and iNOS. For these experiments, fresh-frozen sections of spinal cord adjacent to and in the area of contusion are studied. Quantitative FACS analysis for macrophages (MAC-387) and PMNs (MMP-8) are performed. For these experiments, a 15-mm segment of spinal cord containing the area of contusion is obtained and enzymatically dispersed for FACS analysis; quantitative Western blots for SUR1 and for iNOS. For these experiments, a 15-mm segment of spinal cord containing the area of contusion is obtained and homogenized for Western blotting. Standard methods and materials are used, as described above, including FACS analysis, Western blots and immunofluorescence imaging.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Aguilar-Bryan L, et al., Science. 1995; 268:423-426.
Ammala C, et al., Nature. 1996; 379:545-548.
Anisimov, S. V., et al., Mech. Dev. 117, 25-74 (2002).
Aoki K, et al., Acta Neuropathol (Berl). 2003; 106:121-124.
Arteel G E, et al., Eur J Biochem. 1998; 253:743-750.
Ashcroft F M. Science. 1998; 282:1059-1060.
Ayata, C. & Ropper, A. H. J. Clin. Neurosci. 9, 113-124 (2002).
Babenko A P, et al., Annu Rev Physiol. 1998; 60:667-687.
Ballanyi, K. J. Exp. Biol. 207, 3201-3212 (2004).
Barclay J, et al., J Neurosci. 2002; 22:8139-8147.
Bareyre and Schwab. Trends Neurosci 2003; 26(10):555-563
Bartholdi and Schwab. Eur J Neurosci 1997; 9(7):1422-1438
Baukrowitz T, et al., Science. 1998; 282:1141-1144.
Becker J B, et al., Ann N Y Acad Sci. 2001; 937:172-187.
Beyer C, et al., J Steroid Biochem Mol Biol. 2002; 81:319-325.
Blurton-Jones M, et al., J Comp Neurol. 2001; 433:115-123.
Bussink J, et al., Radiat Res. 2000; 154:547-555.
Cevolani D, et al., Brain Res Bull. 2001; 54:353-361.
Chae Y M et al., Biochem Biophys Res Commun. 319(2): 550-555, 2004.
Chen H., et al., J. Neurol. Sci. 118, 109-6 (1993).
Chen M, et al., J Neurosci. 2003; 23:8568-8577.
Chen M, Simard J M. J Neurosci. 2001; 21:6512-6521
Choi I, et al., Mol Cell Endocrinol. 2001; 181:139-150.
Copin et al., Neurochem Res 1995; 20(1):11-15).
Cress A E. Biotechniques. 2000; 29:776-781.
Currie et al., Brain Res 2000; 863(1-2):169-181.
Dalton et al., Glia 2003; 42(4):325-339.
Dalton S, et al., Glia. 2003; 42:325-339.
Dhandapani K, et al., Endocrine. 2003; 21:59-66.
Dhandapani K M, et al., Biol Reprod. 2002; 67:1379-1385.
Dhandapani K M, et al., BMC Neurosci. 2002; 3:6.
Diab A, et al., Infect Immun. 1999; 67:2590-2601.
Doerfler, A., et al., Stroke 32, 2675-2681 (2001).
Drain P, et al., Proc Natl Acad Sci USA. 1998; 95:13953-13958.
Dubik D et al., Oncogene. 1992; 7:1587-1594.
El Ashry D, et al., J Steroid Biochem Mol Biol. 1996; 59:261-269.
Enkvetchakul D, et al., Biophys J. 2000; 78:2334-2348.
Falk E M, et al., Pharmacol Biochem Behav. 2002; 72:617-622.
Fischer S, et al., J Cell Physiol. 2004; 198:359-369.
Foy M R, et al., Brain Res. 1984; 321:311-314.
Fujita A, et al., Pharmacol Ther. 2000; 85:39-53.
Garcia-Estrada J, et al., Brain Res. 1993; 628:271-278.
Garcia-Ovejero D, et al., J Comp Neurol. 2002; 450:256-271.
Garcia-Segura L M, et al., Prog Neurobiol. 2001; 63:29-60.
Garlid K D, et al., Circ Res. 1997; 81:1072-1082.
Giaccia A J, et al., Int J Radiat Oncol Biol Phys. 1992; 23:891-897.
Gribble, F. M. & Reimann, F. Diabetologia 46, 875-891 (2003).
Grover G J. Can J Physiol Pharmacol. 1997; 75:309-315.
Guo X Z, et al., Cell Res. 2001; 11:321-324.
Hainsworth et al., Neuropharmacology. 2001; 40:784-791.
Hale L P, et al., Am J Physiol Heart Circ Physiol. 2002; 282:H1467-H1477.
Halstead J, et al., J Biol Chem. 1995; 270:13600-13603.
Harder et al., Am J Physiol. 1994; 266:H2098-H2107.
Haruna T, et al., Pflugers Arch. 2000; 441:200-207.
Haug A, et al., Arch Toxicol. 1994; 68:1-7.
Higashijima T, et al., J Biol Chem. 1990; 265:14176-14186.
Higgins C F. Annu Rev Cell Biol. 1992; 8:67-113.
Hiroi H, et al., J Mol Endocrinol. 1999; 22:37-44.
Hobbs M V, et al., J Immunol. 1993; 150:3602-3614.
Hogg et al., FEBS Lett. 2002; 522:125-129.
Hogg et al., Lung. 2002; 180:203-214.
Hohenegger M, et al., Proc Natl Acad Sci U S A. 1998; 95:346-351.
Honda K, et al., J Neurosci Res. 2000; 60:321-327.
Hossain M A, et al., J Biol Chem. 2000; 275:27874-27882.
Hua Y, et al., J Cereb Blood Flow Metab. 2003; 23:1448-1454.
Hunt R A, et al., Hypertension. 1999; 34:603-608.
Huovinen R, et al., Int J Cancer. 1993; 55:685-691.
Ignotz R A, et al., J Cell Biochem. 2000; 78:588-594.
Inagaki N, et al., Neuron. 1996; 16:1011-1017.
Isomoto S, et al., J Biol Chem. 1996; 271:24321-24324.
Jain, Sci. Amer. 271: 58-65, 1994.
Jorgensen M B, et al., Exp Neurol. 1993; 120:70-88.
Jovanovic A, et al., Lab Invest. 1998; 78:1101-1107.
Kakimura et al., FASEB J 2002; 16(6):601-603.
Kakinuma Y, et al., Clin Sci (Lond). 2002; 103 Suppl 48:210S-214S.
Kangas L. Cancer Chemother Pharmacol. 1990; 27:8-12.
Kangas L. J Steroid Biochem. 1990; 36:191-195.
Kanthasamy A, et al., Neuroscience. 2002; 114:917-924.
Karschin, C., et al., FEBS Lett. 401, 59-64 (1997).
Kawamura, S., et al., Acta Neurochir. (Wien.) 109, 126-132 (1991).
Kay et al., J Neurosci Methods. 1986; 16:227-238.
Ke C, et al., Neurosci Lett. 2001; 301:21-24.
Kelly M J, et al., Steroids. 1999; 64:64-75.
Kennedy A S, et al., Int J Radiat Oncol Biol Phys. 1997; 37:897-905.
Kielian T, et al., J Immunol. 2001; 166:4634-4643.
Kimura D. Sci Am. 1992; 267:118-125.
Kohshi K, J Neurol Sci. 2003; 209:115-117.

Koster J C, J Gen Physiol. 1999; 114:203-213.
Kucich U, et al., Arch Biochem Biophys. 2000; 374:313-324.
Kuiper G G, et al., Endocrinology. 1997; 138:863-870.
Kuiper G G, et al., Proc Natl Acad Sci U S A. 1996; 93:5925-5930.
Larsson O, et al., Diabetes. 2000; 49:1409-1412.
Lawson K. Kidney Int. 2000; 57:838-845.
Le Mellay V, et al., J Cell Biochem. 1999; 75:138-146.
Leaney J L, Tinker A. Proc Natl Acad Sci U S A. 2000; 97:5651-5656.
Lee et al., Exp Neurol 2001; 170(1):129-139.
Li, P. A., et al., Neurosci. Lett. 177, 63-65 (1994).
Lieberherr M, et al., J Cell Biochem. 1999; 74:50-60.
Liss B, Roeper J. Mol Membr Biol. 2001; 18:117-127.
Liu Y, et al., Circulation. 1998; 97:2463-2469.
Mateo J, et al., Biochem J. 2003; 376:537-544.
Mathews et al., J Neurosci Methods. 2000; 102:43-51.
Matz et al., Brain Res 1996; 713(1-2):211-222.
Mautes and Noble. Brain Res 2000; 883(2):233-237.
Mautes et al., Exp Neurol 2000; 166(2):254-265.
McNally J G, et al., Methods. 1999; 19:373-385.
Meyer, M., et al., Br. J. Pharmacol. 128, 27-34 (1999).
Moon R C, Constantinou A I. Breast Cancer Res Treat. 1997; 46:181-189.
Moyer et al., J Neurosci Methods. 1998; 86:35-54.
Munoz A, et al., Stroke. 2003; 34:164-170.
Murayama T, et al., J Cell Physiol. 1996; 169:448-454.
Murphy K, et al., Mol Pharmacol. 2003; in press.
Nakabayashi, K. et al. AJNR Am. J. Neuroradiol. 18, 485-491 (1997).
Nichols C G, et al., Science. 1996; 272:1785-1787.
Oehmichen M, et al., Exp Toxicol Pathol. 2000; 52:348-352.
Oehmichen M, et al., Neurotoxicology. 2001; 22:99-107.
Olive P L, et al., Br J Cancer. 2000; 83:1525-1531.
Paczynski R P, et al., Stroke. 2000; 31:1702-1708.
Paech K, et al., Science. 1997; 277:1508-1510.
Panten U, et al., Biochem Pharmacol. 1989; 38:1217-1229.
Papadopoulos et al., Neuroreport 1996; 7(2):429-432.
Papadopoulos M C, et al., Mt Sinai J Med. 2002; 69:242-248.
Perillan P R, et al., J Biol Chem. 2002; 277:1974-1980.
Perillan P R, et al., Glia. 1999; 27:213-225.
Perillan P R, et al., Glia. 2000; 31:181-192.
Phillips M I, Zhang Y C. Methods Enzymol. 2000; 313:46-56.
Piiper A, et al., Am J Physiol. 1997; 272:G135-G140.
Pogue B W, et al., Radiat Res. 2001; 155:15-25.
Proks P, et al., J Physiol. 1999; 514 (Pt 1):19-25.
Qiu J, et al., J Neurosci. 2003; 23:9529-9540.
Rama Rao K V, et al., J Neurosci Res. 2003; 74:891-897.
Rama Rao K V, et al., Neuroreport. 2003; 14:2379-2382.
Ramirez V D, Zheng J. Front Neuroendocrinol. 1996; 17:402-439.
Raucher D, et al., Cell. 2000; 100:221-228.
Regan et al., Neurosci Lett 2000; 282(1-2):1-4.
Robinson A P, et al., Immunology. 1986; 57:239-247.
Robinson S P, et al., Eur J Cancer Clin Oncol. 1988; 24:1817-1821.
Rohacs T, et al., J Biol Chem. 1999; 274:36065-36072.
Rossignol F, et al., Gene. 2002; 299:135-140.
Ruknudin A, et al., J Biol Chem. 1998; 273:14165-14171.
Ruscher K, et al., J Neurosci. 2002; 22:10291-10301.
Russo J, et al., IARC Sci Publ. 1990; 47-78.
Russo J, Russo I H. Lab Invest. 1987; 57:112-137.
Saadoun S, et al., Br J Cancer. 2002; 87:621-623.
Schubert P, et al., Ann N Y Acad Sci. 2000; 903:24-33.
Seidel et al., Cell Tissue Res. 1991; 265:579-587.
Seino, S. Annu. Rev. Physiol 61, 337-362 (1999).
Semenza G L. Biochem Pharmacol. 2000; 59:47-53.
Shaywitz B A, et al., Nature. 1995; 373:607-609.
Shyng S, et al., J Gen Physiol. 1997; 110:643-654.
Singer C A, et al., J Neurosci. 1999; 19:2455-2463.
Singh M, et al., J Neurosci. 1999; 19:1179-1188.
Smith S S, et al., Brain Res. 1987; 422:40-51.
Smith S S, et al., Brain Res. 1988; 475:272-282.
Sohrabji F, et al., Proc Natl Acad Sci U S A. 1995; 92:11110-11114.
Song et al., 2001, J Neurochem 2001; 79(4):804-815.
Stone D J, et al., J Neurosci. 1998; 18:3180-3185.
Streit W J, et al., Prog Neurobiol. 1999; 57:563-581.
Sun M C, et al., J Neurosurg. 2003; 98:565-569.
Sylvia V L, et al, J Steroid Biochem Mol Biol. 2000; 73:211-224.
Teixeira C, et al., Cancer Res. 1995; 55:3902-3907.
Thrash-Bingham C A, et al., J Natl Cancer Inst. 1999; 91:143-151.
Toker A. Curr Opin Cell Biol. 1998; 10:254-261.
Toomey, J. R. et al. Stroke 33, 578-585 (2002).
Toran-Allerand C D. J Steroid Biochem Mol Biol. 1996; 56:169-178.
Tomer L, et al., J Neurosci. 2001; 21:3207-3214.
Treherne, J. M. & Ashford, M. L. Neuroscience 40, 523-531 (1991).
Tucker S J, et al., EMBO J. 1998; 17:3290-3296.
Tucker S J, et al., Nature. 1997; 387:179-183.
U.S. Pat. No. 5,637,085
U.S. Pat. No. 6,391,911
Vogel et al., Stroke. 1999; 30:1134-1141.
Wallace W, et al., Biotechniques. 2001; 31:1076-8, 1080, 1082.
Wang J Y, et al., Glia. 2000; 32:155-164.
Wang Y L. Methods Cell Biol. 1998; 56:305-315.
Wass, C. T. & Lanier, W. L. Mayo Clin. Proc. 71, 801-812 (1996).
Wiesener M S, et al., FASEB J. 2003; 17:271-273.
Woolley C S. Curr Opin Neurobiol. 1999; 9:349-354.
Xie L H, et al., Proc Natl Acad Sci U S A. 1999; 96:15292-15297.
Xu and Giffard. Neurosci Lett 1997; 224(1):9-12.
Yajima Y, et al., Endocrinology. 1997; 138:1949-1958.
Young, W. & Constantini, S. The Neurobiology of Central Nervous System Trauma. Salzman, S. K. & Faden, A. I. (eds.), pp. 123-130 (Oxford University Press, New York, 1994).
Yu et al., Neurosurgery 2001; 49(1):152-158.
Zhang L, et al., Brain Res Mol Brain Res. 2002; 103:1-11.
Zhang Y, et al., J Neurosci. 2001; 21:RC176.
Zheng J, Ramirez V D. J Steroid Biochem Mol Biol. 1997; 62:327-336.
Zunkler, B. J., et al., Biochem. Pharmacol. 67, 1437-1444 (2004).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating a subject at risk for developing a spinal cord injury comprising administering to the subject a compound effective to inhibit a $NC_{Ca-ATP}$ channel in a neuronal cell, a neuroglia cell, a neural endothelial cell or a combination thereof, wherein the compound is glibenclamide, and
wherein the subject is undergoing a surgical treatment or radiation treatment.

2. The method of claim 1, wherein the compound reduces, decreases or inhibits the activation of the $NC_{Ca-ATP}$ channel which reduces an influx of sodium ions ($Na^+$) thereby reducing or preventing depolarization of the cell.

3. The method of claim 1, wherein the compound prevents cytotoxic edema.

4. The method of claim 1, wherein the compound prevents necrotic death.

5. The method of claim 1, wherein the compound prevents or reduces hemorrhagic conversion, extravasated blood, or both near or surrounding a spinal cord injury site.

6. The method of claim 1, wherein the glibenclamide is administered to the subject in a dose in the range of about 0.01 μg/kg/day to about 100 μg/kg/day.

7. The method of claim 1, wherein the compound is administered orally.

8. The method of claim 1, wherein the compound is administered mucosally, intranasally, buccally, rectally, sublingually, intradermally, intramuscularly, intraarterially, intrathecally, subcutaneously, intraperitoneally, or intraventricularly.

9. The method of claim 1, wherein the compound is administered intravenously, mucosally, intranasally, buccally, rectally, sublingually, intradermally, intramuscularly, intraarterially, intrathecally, subcutaneously, intraperitoneally, or intraventricularly.

* * * * *